US009884103B2

(12) United States Patent
Borrego et al.

(10) Patent No.: US 9,884,103 B2
(45) Date of Patent: Feb. 6, 2018

(54) INTERACTIONS OF BETANODAVIRUSES IN INFECTION

(71) Applicant: Elanco Tiergesundheit AG, Indianapolis, IN (US)

(72) Inventors: Juan Jose Borrego, Malaga (ES); Carlos Carballo Perez, Malaga (ES); Maria Del Carmen Alonso, Malaga (ES); Esther Garcia Rosado, Malaga (ES); Benjamin Lopez-Jimena, Malaga (ES); Jose F Rodriguez, St. Catherina (CA)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 14/888,995

(22) PCT Filed: May 26, 2014

(86) PCT No.: PCT/EP2014/060852
§ 371 (c)(1),
(2) Date: Nov. 4, 2015

(87) PCT Pub. No.: WO2014/191363
PCT Pub. Date: Dec. 4, 2014

(65) Prior Publication Data
US 2016/0095915 A1    Apr. 7, 2016

(30) Foreign Application Priority Data

May 28, 2013  (EP) .................................. 13169590.0
May 28, 2013  (EP) .................................. 13169591.8

(51) Int. Cl.
*A61K 39/12*      (2006.01)
*A61K 39/00*      (2006.01)

(52) U.S. Cl.
CPC ...... *A61K 39/12* (2013.01); *A61K 2039/5252* (2013.01); *A61K 2039/552* (2013.01); *C12N 2770/30034* (2013.01)

(58) Field of Classification Search
None
See application file for complete search history.

(56) References Cited

U.S. PATENT DOCUMENTS 9,303,071 B2    4/2016  Simard et al.
2016/0095915 A1*  4/2016  Borrego ................. A61K 39/12
                                                           424/186.1

FOREIGN PATENT DOCUMENTS

WO    WO 2004/074467 A1    9/2004

OTHER PUBLICATIONS

Lauring et al. (Nature Biotechnology. Jun. 2010; 28 (6): 573-579).*
Banu et al. (Bangladesh Journal of Microbiology. Dec. 2007; 24 (2): 100-104).*
Cutrin et al. (Journal of Fish Diseases. 2007; 30: 225-232).*
Panzarin et al. (PloS One. 2016; 11(7): e0158814).*
Sequence alignment of SEQ ID No. 4 nt 604-1030 with geneseq database access No. AXB82808 by Chen et al. in WO2009070929 on Jun. 2009.*
Sequence alignment of SEQ ID No. 4 with GenEmbl database access No. AB0566572 by Iwamoto et al. in 2001 J Gen Virol 82 pt 11 pp. 2653-2662.*
Tanaka S., et al. "Protective immunity of sevenband grouper, *Epinephelus septemfasciatus* Thunberg, against experimental viral nervous necrosis." Journal of Fish Diseases 24.1 (2001): 15-22.
Thiery, R., et al. "Induction of a protective immune response against viral nervous necrosis in the European sea bass *Dicentrarchus labrax* by using betanodavirus virus-like particles." Journal of virology 80.20 (2006): 10201-10207.
Yamashita, H., et al. "Neutralizing antibody levels for protection against betanodavirus infection in sevenband grouper, *Epinephelus septemfasciatus* (Thunberg), immunized with an inactivated virus vaccine." Journal of fish diseases 32.9 (2009): 767-775.
Mori, Koh-ichiro, et al. "Serological relationships among genotypic variants of betanodavirus." Diseases of aquatic organisms 57.1/2 (2003): 19-26.
Lopez-Jimena, B., et al. "A combined RT-PCR and dot-blot hybridization method reveals the coexistence of SJNNV and RGNNV betanodavirus genotypes in wild meagre (*Argyrosomus regius*)." Journal of applied microbiology 109.4 (2010): 1361-1369.
Yamashita, Hirofumi, et al. "The Efficacy of Inactivated Virus Vaccine against Viral Nervous Necrosis (VNN).": Fish Pathology 40.1 (2005): 15-21.
Okinaka Yasushi, and Toshihiro Nakai. "Comparisons among the complete genomes of four betanodavirus genotypes." Diseases of aquatic organisms 80.2 (2008): 113-121.
Nishizawa, Toyohiko, Ryoko Takano, and Kiyokuni Muroga. "Mapping a neutralizing epitope on the coat protein of striped jack nervous necrosis virus." Journal of general virology 80.11 (1999): 3023-3027.
Husgard, Susanna, et al. "Immune response to a recombinant capsid protein of striped jack nervous necrosis virus (SJNNV) in turbot *Scophthalmus maximus* and Atlantic halibut *Hippoglossus hippoglossus*, and evaluation of a vaccine against SJNNV." Diseases of aquatic organisms 45, No. 1 (2001). 33-34.
Tidona, Christian, and Gholamreza Darai. *The Springer index of viruses*. Springer Science & Business Media, (2011).
Ransangan, Julian, et al. "Betanodavirus infection in golden pompano, *Trachinotus blochii*, fingerlings cultured in deep-sea cage culture facility in Langkawi, Malaysia." Aquaculture 315.3 (2011): 327-335.
Iwamoto, Tokinori, et al. "Establishment of an infectious RNA transcription system for Striped jack nervous necrosis virus, the type species of the betanodaviruses." *Journal of General Virology* 82.11 (2001): 2653-2662.

(Continued)

*Primary Examiner* — Shanon A. Foley
(74) *Attorney, Agent, or Firm* — David L. Pflugh

(57) ABSTRACT

Disclosed are interactions between different betanodaviruses during infection of cells "in vitro" and in European sea bass. More specifically, fish administered striped jack nervous necrosis viruses (SJNNV), which are then exposed to red-spotted grouper nervous necrosis viruses (RGNNV), have fewer symptoms of disease associated with RGNNV and/or increased survival as compared to fish not administered SJNNV prior to exposure to RGNNV.

15 Claims, 13 Drawing Sheets

(56) References Cited

OTHER PUBLICATIONS

Ito, Vu, et al. "Variable region of betanodavirus RNA2 is sufficient to determine host specificity." *Diseases of Aquatic organisms* 79.3 (2008): 199-205.

Nishizawa, Toyohiko, et al. "Comparison of the coat protein genes of five fish nodaviruses, the causative agents of viral nervous necrosis in marine fish." *Journal of General Virology* 76.7 (1995): 1563-1569.

Carballo, Carlos, et al. "SJNNV down-regulates RGNNV replication in European sea bass by the induction of the type I interferon system." *Veterinary research* 47.1 (2016): 1-11.

* cited by examiner

Striped Jack nervous necrosis virus genes for protein A, protein B, complete cDNA sequence
GenBank: AB056571.1 (SEQ ID NO: 1).

```
   1 taacatcagc tcttgctctg ttgttttgaa cacttacgca aggttaccgt ttagcataca
  61 atacgacaat tgtaagccat gcgccgcttt gagtttgaac tcgcacgcat gtctggagca
 121 gcattttgtg tcgttacggg ctaccgcctg ttgacatcaa aatggcttgc ggatagggtt
 181 gaggattatc gccaacgtgt cattgcggat cgaaaacaaa ttctccgcga cgcggcggtg
 241 atccgcacga gtatccagaa gcagatggaa ctagtgcgca tttcagtgcg caagggccat
 301 tcccaccagg aggctgctac cgagcggaac agcgctaccg acaccatgat cggtgtggtt
 361 gagaaatgtg gctacgagcc atacattatc tcaccctcac cgcgtgagaa ggagtaccac
 421 gggtcccgtc agttctatag tcttgccgac ttccgtcagg actaccgccg tgatgaaatc
 481 actgaccggc acgttatcgt gatgactgac gttgactatt acgtggatat gcacgaattg
 541 gttggccttg gcgttccgat cctgttgtac acgttccaac ccagcactgt gtccggggaa
 601 gttaaggatg gttattttac cattactgac gaccacgttc actaccgtgt tgctggtggt
 661 aaggacgtgc gccataggat ctggaactac aaccaggata ccatgttcgt gcgctccaaa
 721 ccccgtggtt tctgggcaag tctgaaacag attttgcgcg acattactgg catcaccgct
 781 ttgtgtggct acctctatct caaacttggg atagcccgt tggcgacca ggttacgttg
 841 ttcaccgttg accagttcaa gatgggtgag caccgcaaca tcgtctccat tgttcctttc
 901 gcgacttgtc gctccaacct ccttaagatt agtgagtacg gtgctgaatt ggactacatg
 961 cgttaccaac aacgtaataa taacgccaat ttcaatgctg ttacttacat ctctcaggag
1021 gggcccctga tcagcttggg cctggagggc aatttcgcta gtgtccaact tccgcttcag
1081 gatttcgaaa acatccgtac tgcttatgaa ctgtcgaaga ataacaattt gtcagatact
1141 gttcgtcggt cggcacgttc gtgtaaggag gcagccataa ttcacaaatg ccttcaggcc
1201 gggtgcgatc tcgctagcga ggtcgtccac aagcctggag agctggcacg ccactaccaa
1261 gctcttggtg acacgtacga catcgacccc tctgagcagg gcaaatgcta tgcccgtgag
1321 tacgctcctg ggccgctgac tcaaactgct gtatttccaa gtgagtcgcg ttccaatgag
1381 cttgccacga tcgacggtcg tatagcgggt ccgcaggcta aggcaaagag ccgcgagcac
1441 atcactccaa agatgcacaa agtggctagg gatttcgtgc gccatttggt gcccacggcc
1501 gggctcggcc gtccctatcc cctcacgtat gtcgaagagc accagaccaa gccgttacag
1561 cgggcccgga atgatgctaa tcgatatcac gatgagttca ctatgatcgt caaggcgttc
1621 caaaagaaag aagcatacaa tgccccaaac tatccgcgga acatatcaac tgtcccgcac
1681 acccaaaacg ttaagctgtc cagctacacc tacgctttca agaagcagt cctccagcat
1741 gttccgtggt acatgccaac tcacacaccg gctgaaattg ccgaggctgt gcagagtttg
1801 gccgcaagtt ccactgagct ggttgagact gactatagca aattcgacgg cacgttcctc
1861 cgtttcatgc gggagaatgt cgaatttgcc atttacaagc gttgggtgca cctcgaccat
1921 ttaacagaat tgtccacact attgggaaat gaactccaag cacctgctgt cacccggctg
1981 ggcatcaaat atgacccaga ctgcagtcgt cttagcggtt ccgctctcac gactgacggg
2041 aacagcattg caaatgcttt cgtctcatat cttgccggcc gccaagctgg catggatgat
```

```
2101 gacgaggcat ggacttggat tggtattgtc tacggtgacg acggtcttag atccggaaac
2161 gtgtctgacg cgttgctgtc caaaactgct tcttctctcg gctttgactt gaaaatagtg
2221 aatcgtgcac ctcgcggttc tccagtgacc ttcctctcgc gagtttatct cgatccctgg
2281 tcatcaccgg cttccgtgca gtcgccgttg cgcactttgc tcaaactaca tactacctgt
2341 gacacccaat ctgacatcga agacgtcggg tgggctaaga cgcaggcgta tctagtcact
2401 gactgcttga cacctttat tggccattgg tgtcgggcct accaacgcaa ttgcactgca
2461 cgtgtggtcc aatacgcaga ctacaacgac attccgttct gggttaagaa tgaggatcat
2521 gttggaaact catggcctca gtctgactcc gtcgattgga atgacgttgt tgccaatgag
2581 ctcggcctca ccacagctga gctactcaag cacctcgcgg cgcttgatgc gtatactggt
2641 cccgtgagcg gacttccccg tctgacaaca tcactcgact tggaaccgaa gatgcctgtc
2701 gcattagacg gcgaggtcca agccggtcct agtcaacaac ctcaaactga caaggatgga
2761 acaagtccaa caggcgatcg atcagcacct cgtcgagcta gaacagctct tcaagatgct
2821 gatggacgtg cgtgtcgctc tcggcggagt gaccgtagtc caggtaaacg agatgcgaac
2881 gttcgtgata agcgccagcg ccgcagcaca acgcctccgc gctctcgccc gtcggtaccc
2941 ggcccctcta gcagtggccg cagaaccgat ggagacagag tgagaggagg agctgcacgc
3001 cagcgccagc gacgtcgctc tccagtgtag gcgagtcacc tgcccgctcc taccccccc
3061 ggaccattgg tccctagtc agctttatgc tgtcctacgc ttcggcg
```

Amino acid sequence
Protein A [Striped Jack nervous necrosis virus]
GenBank: BAB64329.1 (SEQ ID NO. 2)

```
   1 mrrfefelar msgaafcvvt gyrlltskwl adrvedyrqr viadrkqilr daavirtsiq
  61 kqmelvrisv rkghshqeaa ternsatdtm igvvekcgye pyiispspre keyhgsrqfy
 121 sladfrqdyr rdeitdrhvi vmtdvdyyvd mhelvglgvp illytfqpst vsgevkdgyf
 181 titddhvhyr vaggkdvrhr iwnynqdtmf vrskprgfwa slkqilrdit gitalcgyly
 241 lklgiapfgd qvtlftvdqf kmgehrnivs ivpfatcrsn llkiseygae ldymryqqrn
 301 nnanfnavty isqegplisl glegnfasvq lplqdfenir tayelsknnn lsdtvrrsar
 361 sckeaaiihk clqagcdlas evvhkpgela rhyqalgdty didpseqgkc yareyapgpl
 421 tqtavfpses rsnelatidg riagpqakak srehitpkmh kvardfvrhl vptaglgrpy
 481 pltyveehqt kplqrarnda nryhdeftmi vkafqkkeay napnyprnis tvphtqnvkl
 541 ssytyafkea vlqhvpwymp thtpaeiaea vqslaasste lvetdyskfd gtflrfmren
 601 vefaiykrwv hldhltelst llgnelqapa vtrlgikydp dcsrlsgsal ttdgnsiana
 661 fvsylagrqa gmdddeawtw igivygddgl rsgnvsdall sktasslgfd lkivnraprg
 721 spvtflsrvy ldpwsspasv qsplrtllkl httcdtqsdi edvgwaktqa ylvtdcltpf
 781 ighwcrayqr nctarvvqya dyndipfwvk nedhvgnswp qsdsvdwndv vanelgltta
 841 ellkhlaald aytgpvsglp rlttsldlep kmpvaldgev qagpsqqpqt dkdgtsptgd
 901 rsaprrarta lqdadgracr srrsdrspgk rdanvrdkrq rrsttpprsr psvpgpsssg
9061 rrtdgdrvrg gaarqrqrrr spv
```

B:

Amino acid sequence
protein B [Striped Jack nervous necrosis virus]
GenBank: BAB64330.1 (SEQ ID NO. 3)

```
   1 meqvqqaidq hlveleqlfk mlmdvrvalg gvtvvqvnem rtfvisasaa aqrlralarr
  61 ypaplavaae pmete
```

Figure 10

Striped Jack nervous necrosis virus gene for coat protein, complete cDNA sequence
GenBank: AB056572.1 (SEQ ID NO. 4)

```
   1 taatctaaca ccgctttgca agtcaaaatg gtacgcaaag gtgataagaa attggcaaaa
  61 cccccgacca caaaggccgc caattctcaa ccacgtcgac gtgcaacaca gcgccgtcgc
 121 agtggtaggg ctgatgcacc cttagctaag gcatcgacta tcacgggatt tggacgtgcg
 181 accaatgatg tccatatctc gggaatgtca cggatcgctc aagcagttgt tccagccggg
 241 acaggaacag atggaaagat tgtcgtcgat tccacaatcg ttccagaact cctgccacgg
 301 cttggacacg ctgctcgaat cttccagcga tacgctgttg aaacactgga gttcgaaatt
 361 cagccaatgt gccccgcaaa cacgggcggt ggttacgttg ctggcttcct gcctgatcca
 421 actgacaacg accacacctt cgatgcgctc aagcaactc gtggtgcagt cgtcgccaaa
 481 tggtgggaaa gtcgaacagt ccggcccag tatactcgaa cgcttctctg gacctcaacc
 541 gggaaggagc agcgattgac atcacctggc cggctggtac tcctgtgtgt tggcagcaac
 601 actgatgttg tcaacgtgtc agtcatgtgt cgctggagcg ttcgccttag tgtcccgtcc
 661 cttgagacac ctgaggacac caccgctcca attactaccc aggcgccact ccacaacgat
 721 tccattaaca acggttacac tggatttcgt tccattctct gggcgcgac ccaactcgac
 781 ctcgctcctg caaacgctgt ctttgtcact gacaaaccgt tgcccattga ttacaatctt
 841 ggagtgggcg acgtcgaccg ggccgtgtac tggcacctgc ggaagaaagc tggagacact
 901 caggtacctg ctgggtactt tgactgggga ctgtgggatg actttaacaa gacattcaca
 961 gttggggcac cctactactc cgaccagcaa ccacggcaaa tcttgctgcc ggctggcacg
1021 ctcttcaccc gtgttgactc ggaaaactaa ccgggtcatc cggatcccta gtgcgtatcg
1081 tggatgacca attcgagaaa ttgattacgg cactaaccac tatcaaaatt gaaattgaca
1141 acaacaagag cgaaattgaa gctatcgcta acaaattaaa cgacaaagca cccaaggagg
1201 gctcgattgc tattgttggt accattgacg gcgtacctgg aacagttgac ggcgcttacc
1261 tcgccgaacc tgtctagcgt gcttgatacg gtgccagctt caccagtctt gtccaacgcc
1321 gaggatttcc ctctttgggc ttgttgggtt accgttagct ccgcgcagtg agcaccaccg
1381 ccatgtggtt aaatggccgc tgatcgccac attactcggc g
```

Figure 11

Amino acid sequence
Coat protein [Striped Jack nervous necrosis virus]
GenBank: BAB64331.1 (SEQ ID NO. 5)

```
  1 mvrkgdkkla kppttkaans qprrratqrr rsgradapla kastitgfgr atndvhisgm
 61 sriaqavvpa gtgtdgkivv dstivpellp rlghaarifq ryavetlefe iqpmcpantg
121 ggyvagflpd ptdndhtfda lqatrgavva kwwesrtvrp qytrtllwts tgkeqrltsp
181 grlvllcvgs ntdvvnvsvm crwsvrlsvp sletpedtta pittqaplhn dsinngytgf
241 rsillgatql dlapanavfv tdkplpidyn lgvgdvdrav ywhlrkkagd tqvpagyfdw
301 glwddfnktf tvgapyysdq qprqillpag tlftrvdsen
```

Figure 12

SEQUENCE LISTING

<160> NUMBER OF SEQ ID NOS: 7

<210> SEQ ID NO 1
<211> LENGTH: 3107

<212> TYPE: DNA
<213> ORGANISM: Striped Jack nervous necrosis virus

<400> SEQUENCE: 1

```
taacatcagc tcttgctctg ttgttttgaa cacttacgca aggttaccgt ttagcataca     60
atacgacaat tgtaagccat gcgccgcttt gagtttgaac tcgcacgcat gtctggagca    120
gcattttgtg tcgttacggg ctaccgcctg ttgacatcaa aatggcttgc ggatagggtt    180
gaggattatc gccaacgtgt cattgcggat cgaaaacaaa ttctccgcga cgcggcggtg    240
atccgcacga gtatccagaa gcagatggaa ctagtgcgca tttcagtgcg caagggccat    300
tcccaccagg aggctgctac cgagcggaac agcgctaccg acaccatgat cggtgtggtt    360
gagaaatgtg gctacgagcc atacattatc tcaccctcac cgcgtgagaa ggagtaccac    420
gggtcccgtc agttctatag tcttgccgac ttccgtcagg actaccgccg tgatgaaatc    480
actgaccggc acgttatcgt gatgactgac gttgactatt acgtggatat gcacgaattg    540
gttggccttg gcgttccgat cctgttgtac acgttccaac ccagcactgt gtccggggaa    600
gttaaggatg gttattttac cattactgac gaccacgttc actaccgtgt tgctggtggt    660
aaggacgtgc gccataggat ctggaactac aaccaggata ccatgttcgt gcgctccaaa    720
ccccgtggtt tctgggcaag tctgaaacag attttgcgcg acattactgg catcaccgct    780
ttgtgtggct acctctatct caaacttggg atagccccgt ttggcgacca ggttacgttg    840
ttcaccgttg accagttcaa gatgggtgag caccgcaaca tcgtctccat tgttcctttc    900
gcgacttgtc gctccaacct ccttaagatt agtgagtacg gtgctgaatt ggactacatg    960
cgttaccaac aacgtaataa taacgccaat ttcaatgctg ttacttacat ctctcaggag   1020
gggcccctga tcagcttggg cctggagggc aatttcgcta gtgtccaact tccgcttcag   1080
gatttcgaaa acatccgtac tgcttatgaa ctgtcgaaga ataacaattt gtcagatact   1140
gttcgtcggt cggcacgttc gtgtaaggag gcagccataa ttcacaaatg ccttcaggcc   1200
gggtgcgatc tcgctagcga ggtcgtccac aagcctggag agctggcacg ccactaccaa   1260
gctcttggtg acacgtacga catcgacccc tctgagcagg gcaaatgcta tgcccgtgag   1320
tacgctcctg ggccgctgac tcaaactgct gtatttccaa gtgagtcgcg ttccaatgag   1380
cttgccacga tcgacggtcg tatagcgggt ccgcaggcta aggcaaagag ccgcgagcac   1440
atcactccaa agatgcacaa agtggctagg gatttcgtgc gccatttggt gcccacggcc   1500
gggctcggcc gtccctatcc cctcacgtat gtcgaagagc accagaccaa gccgttacag   1560
cgggcccgga atgatgctaa tcgatatcac gatgagttca ctatgatcgt caaggcgttc   1620
caaaagaaag aagcatacaa tgccccaaac tatccgcgga acatatcaac tgtcccgcac   1680
acccaaaacg ttaagctgtc cagctacacc tacgctttca aagaagcagt cctccagcat   1740
gttccgtggt acatgccaac tcacacaccg gctgaaattg ccgaggctgt gcagagtttg   1800
gccgcaagtt ccactgagct ggttgagact gactatagca aattcgacgg cacgttcctc   1860
cgtttcatgc gggagaatgt cgaatttgcc atttacaagc gttgggtgca cctcgaccat   1920
ttaacagaat tgtccacact attgggaaat gaactccaag cacctgctgt cacccggctg   1980
ggcatcaaat atgacccaga ctgcagtcgt cttagcggtt ccgctctcac gactgacggg   2040
aacagcattg caaatgcttt cgtctcatat cttgccggcc gccaagctgg catggatgat   2100
gacgaggcat ggacttggat tggtattgtc tacggtgacg acggtcttag atccggaaac   2160
gtgtctgacg cgttgctgtc caaaactgct tcttctctcg gctttgactt gaaaatagtg   2220
```

-continued

```
aatcgtgcac ctcgcggttc tccagtgacc ttcctctcgc gagtttatct cgatccctgg    2280
tcatcaccgg cttccgtgca gtcgccgttg cgcactttgc tcaaactaca tactacctgt    2340
gacacccaat ctgacatcga agacgtcggg tgggctaaga cgcaggcgta tctagtcact    2400
gactgcttga caccttttat tggccattgg tgtcgggcct accaacgcaa ttgcactgca    2460
cgtgtggtcc aatacgcaga ctacaacgac attccgttct gggttaagaa tgaggatcat    2520
gttggaaact catggcctca gtctgactcc gtcgattgga atgacgttgt tgccaatgag    2580
ctcggcctca ccacagctga gctactcaag cacctcgcgg cgcttgatgc gtatactggt    2640
cccgtgagcg gacttccccg tctgacaaca tcactcgact tggaaccgaa gatgcctgtc    2700
gcattagacg gcgaggtcca agccggtcct agtcaacaac ctcaaactga caaggatgga    2760
acaagtccaa caggcgatcg atcagcacct cgtcgagcta gaacagctct tcaagatgct    2820
gatggacgtg cgtgtcgctc tcggcggagt gaccgtagtc caggtaaacg agatgcgaac    2880
gttcgtgata agcgccagcg ccgcagcaca acgcctccgc gctctcgccc gtcggtaccc    2940
ggcccctcta gcagtggccg cagaaccgat ggagacagag tgagaggagg agctgcacgc    3000
cagcgccagc gacgtcgctc tccagtgtag gcgagtcacc tgcccgctcc taccccccc    3060
ggaccattgg tccctagtc agctttatgc tgtcctacgc ttcggcg                   3107
```

<210> SEQ ID NO 2
<211> LENGTH: 983
<212> TYPE: PRT
<213> ORGANISM: Striped Jack nervous necrosis virus

<400> SEQUENCE: 2

```
Met Arg Arg Phe Glu Phe Glu Leu Ala Arg Met Ser Gly Ala Ala Phe
1               5                  10                  15

Cys Val Val Thr Gly Tyr Arg Leu Leu Thr Ser Lys Trp Leu Ala Asp
            20                  25                  30

Arg Val Glu Asp Tyr Arg Gln Arg Val Ile Ala Asp Arg Lys Gln Ile
        35                  40                  45

Leu Arg Asp Ala Ala Val Ile Arg Thr Ser Ile Gln Lys Gln Met Glu
    50                  55                  60

Leu Val Arg Ile Ser Val Arg Lys Gly His Ser His Gln Glu Ala Ala
65                  70                  75                  80

Thr Glu Arg Asn Ser Ala Thr Thr Met Ile Gly Val Val Glu Lys
                85                  90                  95

Cys Gly Tyr Glu Pro Tyr Ile Ile Ser Pro Ser Pro Arg Glu Lys Glu
            100                 105                 110

Tyr His Gly Ser Arg Gln Phe Tyr Ser Leu Ala Asp Phe Arg Gln Asp
        115                 120                 125

Tyr Arg Arg Asp Glu Ile Thr Asp Arg His Val Ile Val Met Thr Asp
    130                 135                 140

Val Asp Tyr Tyr Val Asp Met His Glu Leu Val Gly Leu Gly Val Pro
145                 150                 155                 160

Ile Leu Leu Tyr Thr Phe Gln Pro Ser Thr Val Ser Gly Glu Val Lys
                165                 170                 175

Asp Gly Tyr Phe Thr Ile Thr Asp His Val His Tyr Arg Val Ala
            180                 185                 190

Gly Gly Lys Asp Val Arg His Arg Ile Trp Asn Tyr Asn Gln Asp Thr
        195                 200                 205

Met Phe Val Arg Ser Lys Pro Arg Gly Phe Trp Ala Ser Leu Lys Gln
    210                 215                 220
```

-continued

Ile Leu Arg Asp Ile Thr Gly Ile Thr Ala Leu Cys Gly Tyr Leu Tyr
225                 230                 235                 240

Leu Lys Leu Gly Ile Ala Pro Phe Gly Asp Gln Val Thr Leu Phe Thr
            245                 250                 255

Val Asp Gln Phe Lys Met Gly Glu His Arg Asn Ile Val Ser Ile Val
        260                 265                 270

Pro Phe Ala Thr Cys Arg Ser Asn Leu Leu Lys Ile Ser Glu Tyr Gly
    275                 280                 285

Ala Glu Leu Asp Tyr Met Arg Tyr Gln Gln Arg Asn Asn Asn Ala Asn
290                 295                 300

Phe Asn Ala Val Thr Tyr Ile Ser Gln Glu Gly Pro Leu Ile Ser Leu
305                 310                 315                 320

Gly Leu Glu Gly Asn Phe Ala Ser Val Gln Leu Pro Leu Gln Asp Phe
            325                 330                 335

Glu Asn Ile Arg Thr Ala Tyr Glu Leu Ser Lys Asn Asn Asn Leu Ser
        340                 345                 350

Asp Thr Val Arg Arg Ser Ala Arg Ser Cys Lys Glu Ala Ala Ile Ile
    355                 360                 365

His Lys Cys Leu Gln Ala Gly Cys Asp Leu Ala Ser Glu Val Val His
370                 375                 380

Lys Pro Gly Glu Leu Ala Arg His Tyr Gln Ala Leu Gly Asp Thr Tyr
385                 390                 395                 400

Asp Ile Asp Pro Ser Glu Gln Gly Lys Cys Tyr Ala Arg Glu Tyr Ala
            405                 410                 415

Pro Gly Pro Leu Thr Gln Thr Ala Val Phe Pro Ser Glu Ser Arg Ser
        420                 425                 430

Asn Glu Leu Ala Thr Ile Asp Gly Arg Ile Ala Gly Pro Gln Ala Lys
    435                 440                 445

Ala Lys Ser Arg Glu His Ile Thr Pro Lys Met His Lys Val Ala Arg
450                 455                 460

Asp Phe Val Arg His Leu Val Pro Thr Ala Gly Leu Gly Arg Pro Tyr
465                 470                 475                 480

Pro Leu Thr Tyr Val Glu Glu His Gln Thr Lys Pro Leu Gln Arg Ala
            485                 490                 495

Arg Asn Asp Ala Asn Arg Tyr His Asp Glu Phe Thr Met Ile Val Lys
        500                 505                 510

Ala Phe Gln Lys Lys Glu Ala Tyr Asn Ala Pro Asn Tyr Pro Arg Asn
    515                 520                 525

Ile Ser Thr Val Pro His Thr Gln Asn Val Lys Leu Ser Ser Tyr Thr
530                 535                 540

Tyr Ala Phe Lys Glu Ala Val Leu Gln His Val Pro Trp Tyr Met Pro
545                 550                 555                 560

Thr His Thr Pro Ala Glu Ile Ala Glu Ala Val Gln Ser Leu Ala Ala
            565                 570                 575

Ser Ser Thr Glu Leu Val Glu Thr Asp Tyr Ser Lys Phe Asp Gly Thr
        580                 585                 590

Phe Leu Arg Phe Met Arg Glu Asn Val Glu Phe Ala Ile Tyr Lys Arg
    595                 600                 605

Trp Val His Leu Asp His Leu Thr Glu Leu Ser Thr Leu Leu Gly Asn
610                 615                 620

Glu Leu Gln Ala Pro Ala Val Thr Arg Leu Gly Ile Lys Tyr Asp Pro
625                 630                 635                 640

```
Asp Cys Ser Arg Leu Ser Gly Ser Ala Leu Thr Thr Asp Gly Asn Ser
            645                 650                 655

Ile Ala Asn Ala Phe Val Ser Tyr Leu Ala Gly Arg Gln Ala Gly Met
        660                 665                 670

Asp Asp Asp Glu Ala Trp Thr Trp Ile Gly Ile Val Tyr Gly Asp Asp
    675                 680                 685

Gly Leu Arg Ser Gly Asn Val Ser Asp Ala Leu Leu Ser Lys Thr Ala
690                 695                 700

Ser Ser Leu Gly Phe Asp Leu Lys Ile Val Asn Arg Ala Pro Arg Gly
705                 710                 715                 720

Ser Pro Val Thr Phe Leu Ser Arg Val Tyr Leu Asp Pro Trp Ser Ser
                725                 730                 735

Pro Ala Ser Val Gln Ser Pro Leu Arg Thr Leu Leu Lys Leu His Thr
            740                 745                 750

Thr Cys Asp Thr Gln Ser Asp Ile Glu Asp Val Gly Trp Ala Lys Thr
        755                 760                 765

Gln Ala Tyr Leu Val Thr Asp Cys Leu Thr Pro Phe Ile Gly His Trp
    770                 775                 780

Cys Arg Ala Tyr Gln Arg Asn Cys Thr Ala Arg Val Val Gln Tyr Ala
785                 790                 795                 800

Asp Tyr Asn Asp Ile Pro Phe Trp Val Lys Asn Glu Asp His Val Gly
                805                 810                 815

Asn Ser Trp Pro Gln Ser Asp Ser Val Asp Trp Asn Asp Val Val Ala
            820                 825                 830

Asn Glu Leu Gly Leu Thr Thr Ala Glu Leu Leu Lys His Leu Ala Ala
        835                 840                 845

Leu Asp Ala Tyr Thr Gly Pro Val Ser Gly Leu Pro Arg Leu Thr Thr
    850                 855                 860

Ser Leu Asp Leu Glu Pro Lys Met Pro Val Ala Leu Asp Gly Glu Val
865                 870                 875                 880

Gln Ala Gly Pro Ser Gln Pro Gln Thr Asp Lys Asp Gly Thr Ser
                885                 890                 895

Pro Thr Gly Asp Arg Ser Ala Pro Arg Ala Arg Thr Ala Leu Gln
            900                 905                 910

Asp Ala Asp Gly Arg Ala Cys Arg Ser Arg Arg Ser Asp Arg Ser Pro
        915                 920                 925

Gly Lys Arg Asp Ala Asn Val Arg Asp Lys Arg Gln Arg Ser Thr
    930                 935                 940

Thr Pro Pro Arg Ser Arg Pro Ser Val Pro Gly Pro Ser Ser Ser Gly
945                 950                 955                 960

Arg Arg Thr Asp Gly Asp Arg Val Arg Gly Gly Ala Ala Arg Gln Arg
                965                 970                 975

Gln Arg Arg Arg Ser Pro Val
            980

<210> SEQ ID NO 3
<211> LENGTH: 75
<212> TYPE: PRT
<213> ORGANISM: Striped Jack nervous necrosis virus

<400> SEQUENCE: 3

Met Glu Gln Val Gln Gln Ala Ile Asp Gln His Leu Val Glu Leu Glu
1               5                   10                  15

Gln Leu Phe Lys Met Leu Met Asp Val Arg Val Ala Leu Gly Gly Val
            20                  25                  30
```

```
Thr Val Val Gln Val Asn Glu Met Arg Thr Phe Val Ile Ser Ala Ser
        35                  40                  45

Ala Ala Ala Gln Arg Leu Arg Ala Leu Ala Arg Arg Tyr Pro Ala Pro
    50                  55                  60

Leu Ala Val Ala Ala Glu Pro Met Glu Thr Glu
65                  70                  75

<210> SEQ ID NO 4
<211> LENGTH: 1421
<212> TYPE: DNA
<213> ORGANISM: Striped Jack nervous necrosis virus

<400> SEQUENCE: 4
taatctaaca ccgctttgca agtcaaaatg gtacgcaaag gtgataagaa attggcaaaa      60
cccccgacca caaaggccgc caattctcaa ccacgtcgac gtgcaacaca gcgccgtcgc     120
agtggtaggg ctgatgcacc cttagctaag gcatcgacta tcacgggatt tggacgtgcg     180
accaatgatg tccatatctc gggaatgtca cggatcgctc aagcagttgt tccagccggg     240
acaggaacag atggaaagat tgtcgtcgat tccacaatcg ttccagaact cctgccacgg     300
cttggacacg ctgctcgaat cttccagcga tacgctgttg aaacactgga gttcgaaatt     360
cagccaatgt gccccgcaaa cacgggcggt ggttacgttg ctggcttcct gcctgatcca     420
actgacaacg accacacctt cgatgcgctc caagcaactc gtggtgcagt cgtcgccaaa     480
tggtgggaaa gtcgaacagt ccggccccag tatactcgaa cgcttctctg gacctcaacc     540
gggaaggagc agcgattgac atcacctggc cggctggtac tcctgtgtgt tggcagcaac     600
actgatgttg tcaacgtgtc agtcatgtgt cgctggagcg ttcgccttag tgtcccgtcc     660
cttgagacac ctgaggacac caccgctcca attactaccc aggcgccact ccacaacgat     720
tccattaaca acggttacac tggatttcgt tccattctct tgggcgcgac ccaactcgac     780
ctcgctcctg caaacgctgt ctttgtcact gacaaaccgt tgcccattga ttacaatctt     840
ggagtgggcg acgtcgaccg ggccgtgtac tggcacctgc ggaagaaagc tggagacact     900
caggtacctg ctgggtactt tgactgggga ctgtgggatg actttaacaa gacattcaca     960
gttggggcac cctactactc cgaccagcaa ccacggcaaa tcttgctgcc ggctggcacg    1020
ctcttcaccc gtgttgactc ggaaaactaa ccgggtcatc cggatcccta gtgcgtatcg    1080
tggatgacca attcgagaaa ttgattacgg cactaaccac tatcaaaatt gaaattgaca    1140
acaacaagag cgaaattgaa gctatcgcta acaaattaaa cgacaaagca cccaaggagg    1200
gctcgattgc tattgttggt accattgacg gcgtacctgg aacagttgac ggcgcttacc    1260
tcgccgaacc tgtctagcgt gcttgatacg gtgccagctt caccagtctt gtccaacgcc    1320
gaggatttcc ctctttgggc ttgttgggtt accgttagct ccgcgcagtg agcaccaccg    1380
ccatgtggtt aaatggccgc tgatcgccac attactcggc g                        1421

<210> SEQ ID NO 5
<211> LENGTH: 340
<212> TYPE: PRT
<213> ORGANISM: Striped Jack nervous necrosis virus

<400> SEQUENCE: 5

Met Val Arg Lys Gly Asp Lys Lys Leu Ala Lys Pro Pro Thr Thr Lys
1               5                   10                  15

Ala Ala Asn Ser Gln Pro Arg Arg Arg Ala Thr Gln Arg Arg Arg Ser
            20                  25                  30
```

```
Gly Arg Ala Asp Ala Pro Leu Ala Lys Ala Ser Thr Ile Thr Gly Phe
         35                   40                  45

Gly Arg Ala Thr Asn Asp Val His Ile Ser Gly Met Ser Arg Ile Ala
     50                  55                  60

Gln Ala Val Val Pro Ala Gly Thr Gly Thr Asp Gly Lys Ile Val Val
 65                  70                  75                  80

Asp Ser Thr Ile Val Pro Glu Leu Leu Pro Arg Leu Gly His Ala Ala
                 85                  90                  95

Arg Ile Phe Gln Arg Tyr Ala Val Glu Thr Leu Glu Phe Glu Ile Gln
             100                 105                 110

Pro Met Cys Pro Ala Asn Thr Gly Gly Tyr Val Ala Gly Phe Leu
             115                 120                 125

Pro Asp Pro Thr Asp Asn Asp His Thr Phe Asp Ala Leu Gln Ala Thr
         130                 135                 140

Arg Gly Ala Val Val Ala Lys Trp Trp Glu Ser Arg Thr Val Arg Pro
145                 150                 155                 160

Gln Tyr Thr Arg Thr Leu Leu Trp Thr Ser Thr Gly Lys Glu Gln Arg
                 165                 170                 175

Leu Thr Ser Pro Gly Arg Leu Val Leu Leu Cys Val Gly Ser Asn Thr
             180                 185                 190

Asp Val Val Asn Val Ser Val Met Cys Arg Trp Ser Val Arg Leu Ser
             195                 200                 205

Val Pro Ser Leu Glu Thr Pro Glu Asp Thr Thr Ala Pro Ile Thr Thr
         210                 215                 220

Gln Ala Pro Leu His Asn Asp Ser Ile Asn Asn Gly Tyr Thr Gly Phe
225                 230                 235                 240

Arg Ser Ile Leu Leu Gly Ala Thr Gln Leu Asp Leu Ala Pro Ala Asn
                 245                 250                 255

Ala Val Phe Val Thr Asp Lys Pro Leu Pro Ile Asp Tyr Asn Leu Gly
             260                 265                 270

Val Gly Asp Val Asp Arg Ala Val Tyr Trp His Leu Arg Lys Lys Ala
         275                 280                 285

Gly Asp Thr Gln Val Pro Ala Gly Tyr Phe Asp Trp Gly Leu Trp Asp
     290                 295                 300

Asp Phe Asn Lys Thr Phe Thr Val Gly Ala Pro Tyr Tyr Ser Asp Gln
305                 310                 315                 320

Gln Pro Arg Gln Ile Leu Leu Pro Ala Gly Thr Leu Phe Thr Arg Val
                 325                 330                 335

Asp Ser Glu Asn
         340

<210> SEQ ID NO 6
<211> LENGTH: 23
<212> TYPE: DNA
<213> ORGANISM: Artificial Sequence
<220> FEATURE:
<223> OTHER INFORMATION: oligo

<400> SEQUENCE: 6
gacaccaccg ctccaattac tac                                         23

<210> SEQ ID NO 7
<211> LENGTH: 23
<212> TYPE: DNA
<213> ORGANISM: Artificial Sequence
<220> FEATURE:
```

```
<223> OTHER INFORMATION: oligo

<400> SEQUENCE: 7
acgaaatcca gtgtaaccgt tgt                                              23
```

INTERACTIONS OF BETANODAVIRUSES IN INFECTION

The present application is a national phase entry under 35 U.S.C. §371 of International Patent Application PCT/EP2014/060852, filed on May 26, 2014 and published in English as International Patent. Publication WO2014/191363 A1 on Dec. 4, 2014, which claims benefit of priority to European Patent Application Ser. Nos. 13169590.0, filed May 28, 2013, and 13169591.8, filed May 28, 2013; all of which are incorporated by reference in their entirety.

FIELD OF THE INVENTION

The present invention generally relates to Striped jack nervous necrosis virus (SJNNV) for use in protecting fish against disease associated with Red-spotted grouper nervous necrosis virus (RGNNV) infection. In another aspect the invention relates to a method for protecting fish against disease associated with RGNNV infection, comprising administering SJNNV to the fish, where the fish subsequently exposed to the RGNNV have fewer and/or reduced symptoms of disease as compared to fish which are exposed to RGNNV in absence of prior administration of SJNNV.

BACKGROUND OF THE INVENTION

Viruses of the family Nodaviridae, genus *Betanodavirus* (i.e., betanodaviruses) infect many different marine and freshwater fish species worldwide and are the etiological agents of viral encephalopathy and retinopathy (VER) in fish. This disease, also called viral nervous necrosis (VNN), can cause significant fish mortality.

The betanodaviruses that cause the disease are non-enveloped and their genomes contain two single-stranded, positive-sense RNA molecules, designated RNA1 and RNA2. Infected cells contain three ssRNAs: RNA1, RNA2 and subgenomic RNA3 derived from RNA1. The T4 variable region within the RNA2 segment has been used to classify betanodaviruses into four different genotypes: striped jack nervous necrosis virus (SJNNV), tiger puffer nervous necrosis virus (TPNNV), barfin flounder nervous necrosis virus and red-spotted grouper nervous necrosis virus (RGNNV) (Nishizawa et al. 1997). The NNV part of the name refers to nervous necrosis virus and the initial part of the name refers to the fish from which it was isolated. These have become accepted species, with the Striped jack species being known as the type species, based on the characterisation of the SJNag93 isolate. (Iwamoto et al, 2001) Others which may be members of the genus *Betanodavirus*, but have not yet been approved as separate species, and may or may not be variants of any of the four accepted species listed above include: Atlantic cod nervous necrosis virus, Atlantic halibut nodavirus, *Dicentrarchus labrax encephalitis* virus, Dragon grouper nervous necrosis virus, Greasy grouper nervous necrosis virus, Japanese flounder nervous necrosis virus, *Lates calcarifer* encephalitis virus, Malabaricus grouper nevous necrosis virus, Seabass nervous necrosis virus, *Solea senegalensis* nervous necrosis virus and Turbot nodavirus. (Virus Taxonomy, 2012).

Different genotypes of betanodaviruses likely infect different host ranges of fish. However, coexistence of SJNNV and RGNNV, within single fish in the wild, has been shown in wild meager (*Argyrosomus regius*). Genetic analysis based on both RNA1 and RNA2 has also demonstrated the existence of reassortant viruses (RGNNV/SJNNV and SJNNV/RGNNV) in infected fish. Such reassortant virus strains or isolates, containing one genome RNA molecule from SJNNV and one genome RNA molecule from RGNNV, have been isolated from Senegalese sole and gilt-head sea bream. Reassortant strains have been associated with clinical outbreaks of disease. Reassortants could result from coinfection of the same cells with SJNNV and RGNNV. Although this evidence indicates that both SJNNV and RGNNV RNA can coexist in the same infected cells, nothing is known about how this affects replication and/or progeny virus production, or how it affects the ability to cause symptoms of disease.

SJNNV and RGNNV have separately been detected in fish species inhabiting the Iberian Peninsula, such as European sea bass (*Dicentrarchus labrax*), Senegalese sole (*Solea senegalensis*), gilt-head seabream (*Sparus aurata*), red-banded seabream (*Pagrus auriga*), common seabream (*Pagrus pagrus*), Shi drum, (*Umbrina cirrosa*) and white seabream (*Diploidus sargus*).

The RGNNV genotype appears to be the most common in the Mediterranean region and has been responsible for devastating losses in the fishing industry, especially in Greece. The losses in the field of European sea bass have been reported to be up to 60%. Hence there is an urgent need for ways to protect fish, especially sea bream, from the effects of RGNNV infection.

SUMMARY

In a first aspect, the invention relates to Striped jack nervous necrosis virus (SJNNV) for use in protecting fish against disease associated with Red-spotted grouper nervous necrosis virus (RGNNV) infection.

In a preferred embodiment the SJNNV is
i) SJNNV with a nucleotide or amino acid sequence which is preferably at least 90% identical, more preferably at least 95% identical, particularly preferably at least 97% identical, more particularly preferably at least 99% identical with the nucleotide or amino acid sequence of SJNNV isolate SJNag93, or ii) SJNNV which serologically reacts with antiserum to isolate SJNag93 or iii) SJNNV with a nucleotide or amino acid sequence which is preferably at least 90% identical, more preferably at least 95% identical, particularly preferably at least 97% identical, more particularly preferably at least 99% identical with the nucleotide or amino acid sequence of SJNNV isolate SJNag93 and serologically reacts with antiserum to isolate SJNag93.

In a further preferred embodiment the percentage identity of the nucleotide or amino acid sequence of SJNNV is relative to the T4 variable region within the RNA2 segment of SJNNV isolate SJNag93.

In a more preferred embodiment the percentage identity of the nucleotide sequence of SJNNV is relative to the sequence from nucleotides 604 to 1030 of RNA2 of SJNag93 SJNNV, or the percentage identity of the amino acid sequence of SJNNV is relative to amino acids 204 to 331 of the protein encoded by RNA2 of SJNag93 SJNNV, preferably from amino acids 223 to 331 of the protein encoded by RNA2 of SJNag93 SJNNV, more preferably from amino acids 235 to 315 of the protein encoded by RNA2 of SJNag93 SJNNV.

Preferably the SJNNV is selected from the group consisting of SJNag93, Jp/06/SJ, SJOri, SJ91 Nag, SJ92Nag, SJ94Nag and RS95Hir 3, preferably SJNag93.

In a preferred embodiment the SJNNV is administered to the fish in an amount of at least about $1\times10^4$ TCID$_{50}$/fish.

Also preferably, protecting fish against disease involves reducing the mortality in a fish population that results from a RGNNV infection.

Furthermore preferably the fish is selected from the group consisting of European sea bass, Senegalese sole, gilt-head sea bream, red-banded seabream, common seabream, white seabream and wild meager, preferably European sea bass.

In a further preferred embodiment, the RGNNV is i) RGNNV with a nucleotide or amino acid sequence which is preferably at least 90% identical, more preferably at least 95% identical, particularly preferably at least 97% identical, more particularly preferably at least 99% identical with RGNNV isolate ERV378/102-5/04, or ii) RGNNV which serologically reacts with antiserum to isolate ERV378/102-5/04, or iii) RGNNV with a nucleotide or amino acid sequence which is preferably least 90% identical, more preferably at least 95% identical, particularly preferably at least 97% identical, more particularly preferably at least 99% identical with the nucleotide or amino acid sequence of RGNNV isolate ERV378/102-5/04 and serologically reacts with antiserum to isolate ERV378/102-5/04.

In a preferred embodiment the percentage identity of the nucleotide or amino acid sequence of RGNNV is relative to the T4 variable region within the RNA2 segment of RGNNV isolate ERV378/102-5/04.

In yet another preferred embodiment the invention relates to SJNNV for use comprising administering SJNNV to the fish, where the fish subsequently exposed to the RGNNV have fewer and/or reduced symptoms of disease as compared to fish which are exposed to RGNNV in absence of prior administration of SJNNV.

In another aspect the invention relates to SJNNV for use against viral nervous necrosis or viral encephalopathy and retinopathy in fish caused by RGNNV infection.

In yet another aspect the invention relates to a method for protecting fish against disease associated with RGNNV infection, comprising administering SJNNV to the fish, where the fish subsequently exposed to the RGNNV have fewer and/or reduced symptoms of disease as compared to fish which are exposed to RGNNV in absence of prior administering of SJNNV.

In a preferred embodiment the SJNNV is used to decrease mortality of fish, preferably sea bass, which are later exposed to RGNNV, compared to fish, preferably sea bass, that have not been administered with the SJNNV or a virus which is preferably at least 90% identical, more preferably at least 95% identical, particularly preferably at least 97% identical, more particularly preferably at least 99% identical with SJNNV isolate SJNag93.

In another preferred aspect of the invention there is provided method for reducing mortality in fish, preferably sea bass, that is associated with RGNNV infection, comprising inoculating the fish, preferably sea bass, with SJNNV, wherein the fish, preferably sea bass, which are subsequently exposed to a strain or strains of RGNNV, that is capable of causing mortality, have a reduced mortality rate as compared to sea bass that have not been inoculated with the SJNNV and are exposed to that strain or strains of RGNNV.

Preferably in the method according to the invention the RGNNV is capable of causing mortality in the fish. Preferably also the fish administered the SJNNV and subsequently exposed to the RGNNV have lower mortality as compared to fish exposed to RGNNV in absence of prior administering of SJNNV.

In a preferred embodiment of the method of the invention the fish are exposed to the RGNNV up to about 6 weeks after administering the SJNNV. More preferably the fish are exposed to the RGNNV up to about 3 weeks after administering the SJNNV. Especially preferably the fish are exposed to the RGNNV up to about 72 hours after administering the SJNNV. More especially preferably the fish are exposed to the RGNNV up to about 24 hours after administering the SJNNV. In another preferred embodiment the SJNNV includes isolate SJ93Nag. In yet another preferred embodiment where the SJNNV and the RGNNV are capable of infecting the same species of fish, which preferably include European sea bass, Senegalese sole, gilt-head sea bream, red-banded seabream, common seabream, white seabream and wild meager. In another preferred embodiment of the method of the invention administering of the SJNNV is performed by intramuscular or peritoneal injection of the fish with the virus or immersion of fish in a bath containing the virus. In yet another preferred embodiment of the method of the invention an amount of the SJNNV administered to the fish is at least about $1\times10^4$ $TCID_{50}$/fish. More preferably the amount of the SJNNV administered to the fish is between about $1\times10^4$ and about $1.5\times10^4$ $TCID_{50}$/fish. In a preferred embodiment of the method of the invention administering of the SJNNV results in increased transcriptional expression of at least one interferon-inducible gene, where preferably the interferon-inducible gene includes Mx. Preferably in the method according to the invention the sea bass that are inoculated with SJNNV and subsequently exposed to RGNNV have a reduced mortality rate for up to about 72 hours after inoculation with SJNNV.

In a preferred embodiment of the method according to the invention the SJNNV is i) SJNNV with a nucleotide or amino acid sequence which is preferably at least 90% identical, more preferably at least 95% identical, particularly preferably at least 97% identical, more particularly preferably at least 99% identical with the nucleotide or amino acid sequence of SJNNV isolate SJNag93, or ii) SJNNV which serologically reacts with antiserum to isolate SJNag93 or iii) SJNNV with a nucleotide or amino acid sequence which is preferably least 90% identical, more preferably at least 95% identical, particularly preferably at least 97% identical, more particularly preferably at least 99% identical with the nucleotide or amino acid sequence of SJNNV isolate SJNag93 SJNNV and serologically reacts with antiserum to isolate SJNag93.

In a preferred embodiment of the method according to the invention the percentage identity of the nucleotide or amino acid sequence is relative to the T4 variable region within the RNA2 segment of SJNNV isolate SJNag93.

In a further preferred embodiment of the method according to the invention the RGNNV has a nucleotide or amino acid sequence which is preferably at least 90% identical, more preferably at least 95% identical, particularly preferably at least 97% identical, more particularly preferably at least 99% identical with RGNNV isolate ERV378/102-5/04 or ii) RGNNV which serologically reacts with antiserum to isolate ERV378/102-5/04 or iii) RGNNV with a nucleotide or amino acid sequence which is preferably least 90% identical, more preferably at least 95% identical, particularly preferably at least 97% identical, more particularly preferably at least 99% identical with the nucleotide or amino acid sequence of RGNNV isolate ERV378/102-5/04 and serologically reacts with antiserum to isolate ERV378/102-5/04.

In a preferred embodiment of the method according to the invention the percentage identity of the nucleotide or amino acid sequence is relative to the T4 variable region within the RNA2 segment of RGNNV isolate ERV378/102-5/04.

In yet another preferred embodiment of the invention the RGNNV has a nucleotide sequence which is preferably at least 90% identical, more preferably at least 95% identical, particularly preferably at least 97% identical, more particularly preferably at least 99% identical with RGNNV RNA1 and RNA2. A representative example of RGNNV RNA1 is to be found in Genbank under the accession number NC_008040.1. A representative example of RGNNV RNA2 is to be found in Genbank under the accession number NC_008041.1.

In a preferred embodiment the percentage identity of the nucleotide sequence is relative to the T4 variable region within the RNA2 segment of RGNNV. A representative example of RGNNV RNA2 is to be found in Genbank under the accession number NC_008041.1.

In another aspect the invention relates to a vaccine comprising SJNNV for use in preventing or treating RGNNV infection in fish. In yet another aspect the invention relates to a vaccine for use in protecting fish against viral nervous necrosis or viral encephalopathy and retinopathy in fish caused by RGNNV infection, wherein the vaccine comprises SJNNV.

Preferably in said vaccine the SJNNV is
i) SJNNV with a nucleotide or amino acid sequence which is preferably at least 90% identical, more preferably at least 95% identical, particularly preferably at least 97% identical, more particularly preferably at least 99% identical with the nucleotide or amino acid sequence of SJNNV isolate SJNag93,
or ii) SJNNV which serologically reacts with antiserum to isolate SJNag93
or iii) SJNNV with a nucleotide or amino acid sequence which is preferably least 90% identical, more preferably at least 95% identical, particularly preferably at least 97% identical, more particularly preferably at least 99% identical with the nucleotide or amino acid sequence of SJNNV isolate SJNag93 and serologically reacts with antiserum to isolate SJNag93. More preferably the percentage identity of the nucleotide or amino acid sequence of the SJNNV is relative to the T4 variable region within the RNA2 segment of SJNNV isolate SJNag93. In a preferred embodiment of the vaccine the SJNNV is administered to the fish in an amount of at least about $1\times10^4$ TCID$_{50}$/fish. In another preferred embodiment of the vaccine SJNNV RNA2 is administered to the fish. Preferably also the SJNNV is composed of SJNNV RNA1 and SJNNV RNA2. In an alternate embodiment, the SJNNV is SJNNV RNA2, without SJNNV RNA1. In a preferred embodiment of the vaccine the SJNNV is in the form of a heat killed or chemically inactivated SJNNV. Typically the chemically inactivated SJNNV is inactivated using an aziridine compound, preferably binary ethyleneimine. Preferably the SJNNV is administered in the form of a DNA or RNA vaccine, preferably RNA vaccine. In a another preferred embodiment of the vaccine according to the invention, the fish is selected from the group consisting of European sea bass, Senegalese sole, gilt-head sea bream, red-banded seabream, common seabream, white seabream and wild meager, preferably European sea bass. Preferably also in the vaccine according to the invention the SJNNV is selected from the group consisting of SJNag93, Jp/06/SJ, SJOri, SJ91Nag, SJ92Nag, SJ94Nag and RS95Hir 3, preferably SJNag93.

In another aspect the invention relates to the use of SJNNV in the manufacture of a composition for reducing the amount of mortality in fish that results from infection with RGNNV.

In yet another aspect the invention relates to a method for inhibiting replication of SJNNV in cells, comprising infecting cells with RGNNV prior to, or simultaneously with, infecting the cells with SJNNV.

A further aspect of the invention relates to a method for infecting fish with viruses, comprising:
a) administering SJNNV to the fish; and
b) exposing the fish to RGNNV;
wherein the fish have fewer and/or reduced symptoms that are associated with RGNNV infection than do fish exposed to RGNNV that have not been administered SJNNV.

In yet a further aspect the invention relates to a method for stimulating replication of RGNNV in cells, comprising infecting cells with SJNNV prior to, or simultaneously with, infecting the cells with RGNNV.

BRIEF DESCRIPTION OF THE DRAWINGS

In the accompanying drawings, which are incorporated in and constitute a part of the specification, embodiments of, or related to, methods and compositions are illustrated, which, together with the detailed description given below, serve to describe the examples. It should be appreciated that the embodiments illustrated in the drawings are shown for the purpose of illustration and not for limitation. It should be appreciated that changes, modifications and deviations from the embodiments illustrated in the drawings may be made without departing from the spirit and scope of the invention, as disclosed below.

FIG. 2 illustrates example data from a study where different strains and inoculums of RGNNV were administered to sea bass and fish mortality was followed. Positive control is RGNNV isolate ERV378/102-5/04.

FIG. 3 illustrates example data from a study where an RGNNV strain was administered to sea bass of different weights and fish mortality was followed.

FIG. 5 illustrates example data from a study where RGNNV genome RNA was quantified at various times after fish infected with SJNNV had been superinfected with RGNNV. First column at each time point is the RG control group (group 3) and second column at each time point is the SJ/RG group (group 4).

cells infected with SJNNV were superinfected with RGNNV, and (C) cells infected with RGNNV were superinfected with SJNNV.

Figure 8:
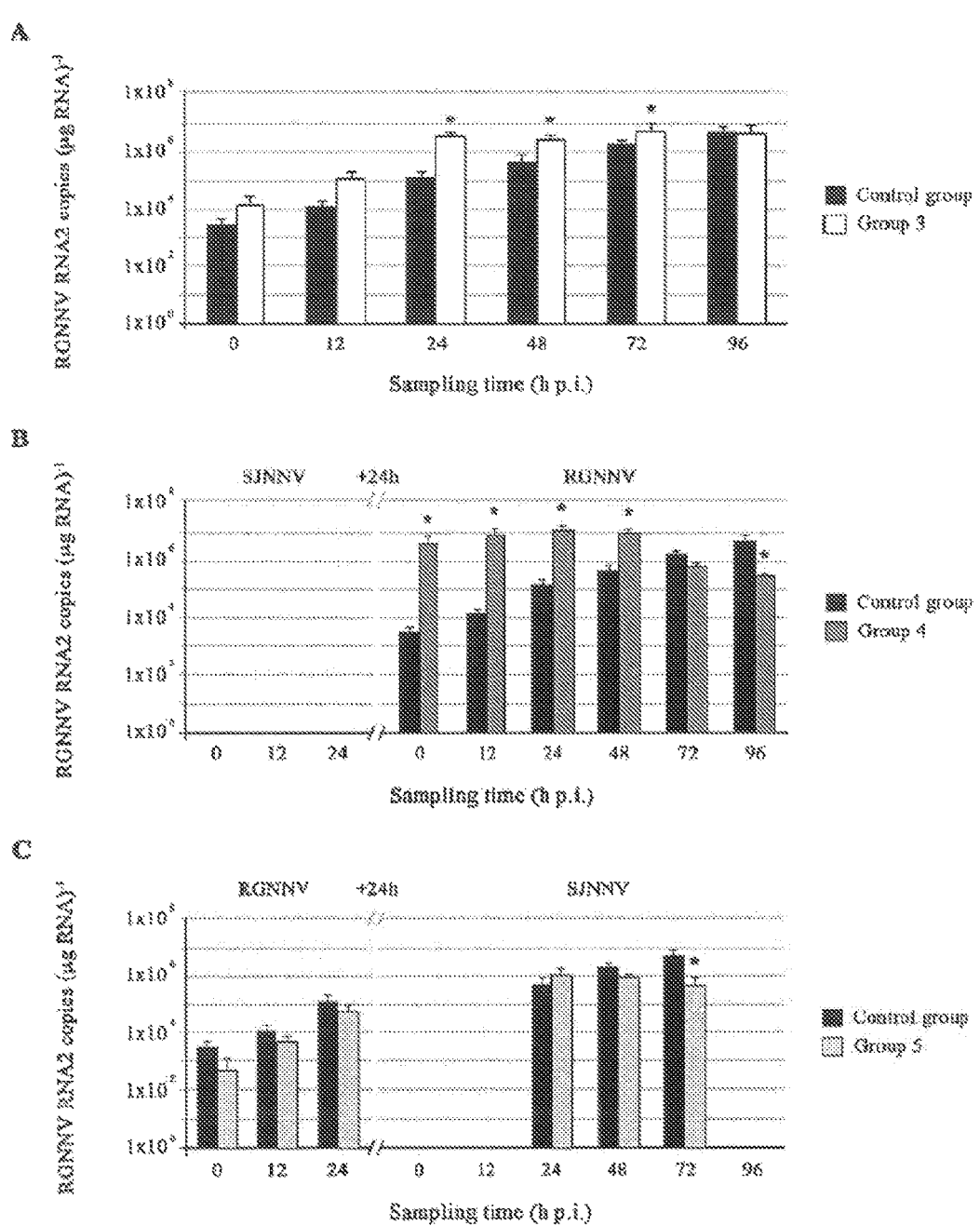

FIG. 8 illustrates example data from studies where RGNNV genome RNA was quantified at various times after: (A) cells were coinfected with SJNNV and RGNNV, (B) cells infected with SJNNV were superinfected with RGNNV, and (C) cells infected with RGNNV were superinfected with SJNNV.

FIG. 9 SJNNV RNA 1 (SEQ ID No. 1) Striped Jack nervous necrosis virus gene for protein A and protein B, complete cds, nucleotide sequence FIG. 10a SJNNV RNA 1 (SEQ ID No. 2) Amino acid sequence of protein A FIG. 10b SJNNV RNA 1 (SEQ ID No. 3) Amino acid sequence of protein B FIG. 11 SJNNV RNA 2 (SEQ ID No 4) Striped Jack nervous necrosis virus gene for coat protein, complete cds, nucleotide sequence FIG. 12 SJNNV RNA 2 (SEQ ID No 5). Amino acid sequence of coat protein

DETAILED DESCRIPTION

Herein, "SJNNV" means a *betanodavirus* of the striped jack nervous necrosis virus species or genotype. The SJNNV viruses disclosed herein are generally able to infect, or at least adsorb to, at least some of the same cells as some viruses of the RGNNV species or genotype. Example of SJNNV isolates include, but are not limited to, SJ93Nag, Jp/06/SJ, SJOri, SJ91Nag, SJ92Nag, SJ94Nag and RS95Hir. A preferred example of an SJNNV is isolate SJ93Nag. (See Genbank sequence AB056571, FIG. 9: SEQ ID No. 1 (RNA 1: virus genes for protein A, protein B), FIG. 10a: SEQ ID NO. 2: Amino acid sequence of protein A [Striped Jack nervous necrosis virus] GenBank: BAB64329, FIG. 10b: SEQ ID NO. 3: Amino acid sequence of protein B [Striped Jack nervous necrosis virus] GenBank: BAB64330. FIG. 11 SEQ ID No 4 Striped Jack nervous necrosis virus gene for coat protein, complete cds GenBank: AB056572. FIG. 12 SEQ ID No 5. Amino acid sequence of Striped Jack nervous necrosis virus gene for coat protein, complete cds GenBank: BAB64331)

Herein, "RGNNV" means a *betanodavirus* of the red-spotted grouper nervous necrosis virus species or genotype. The RGNNV viruses disclosed herein are generally able to infect, or at least adsorb to, at least some of the same cells as some viruses of the SJNNV genotype. Examples of RGNNV isolates include, but are not limited to ERV378/102-5/04, SpDI-IAusc1688.08, Mt/01/Sba, Gr/02/Sba, Gr/12/Sba, Pt/08/Sba, It/23/Sba, It/24/Sdr, It/19/Sba, Jp/15/Rp, Th/07/Bgr, Sg/14/Bar, Sp/20/Sba, Gr/16/Sba, SGWak97, SGMie95, RGOka94, JSOit98, KGOit97, HG0001, BGThA99, SBGre96, WSBUS99A, WSBUS99B, BAus94, JFHir92, JFHir96, JF93Hir, MR94Tha, RG94Oka, JF94Wak, JF95Oit, RG91Tok, SB95Ita, SG94Oit, JF95Tok, JS95Shi, JF95Sag, PA94Oit and KG95Olt. A preferred example of an RGNNV is isolate is ERV378/102-5/04 or SpDI-IAusc1688.08, particularly preferably ERV378/102-5/04.

Herein, "fish," generally refers to species of fish that can be infected by SJNNV and RGNNV. These species may include, but may not be limited to, European sea bass, Senegalese sole, gilt-head seabream, red-banded seabream, common seabream, white seabream Shi drum, and wild meager.

Herein, "capable of causing," generally as referred to viruses, means that a virus can produce the specified effect (e.g., symptoms and/or disease, and/or mortality) under at least certain conditions or circumstances.

Herein, "symptoms," refers to observable and/or measurable characteristics of or in an animal that are generally thought not to be normal for a healthy animal. Symptoms may be indicative of disease. Herein, the animal will generally be a fish and symptoms may be changes in characteristics of fish (e.g., physical changes, behavioral changes, etc.) that are different than what are thought to be normal or healthy characteristics. Herein, symptoms may be attributed to or considered to be caused by infection with a virus. For example, betanodaviruses can be the cause of viral nervous necrosis (VNN) in fish. Symptoms of VNN may include vacuolation in cells of the retina and central nervous system neuronal degeneration in the central nervous system (CNS), anorexia, abnormalities in pigmentation, sight, bladder control and swim behavior. VNN caused by betanodaviruses may result in death of infected fish. Mortality, therefore, could be considered to be a symptom of VNN, although mortality may be referred to as a result of VNN. Symptoms may be referred to using other terms, such as clinical signs, manifestations of disease, and the like.

Herein, "reducing symptoms," "reducing mortality," "reducing mortality rate," and the like, generally refer to comparison of properties in different fish, or different groups of fish, where the extent of the observed properties in one group of fish is decreased or reduced in another group. Generally, the decrease can be attributed to an action or characteristic. Herein, for example, a population of fish infected with RGNNV generally will display symptoms due to infection with RGNNV. A measurable number of the infected fish may die. The number of fish in a comparable population that display the symptoms or die, where the fish have been administered SJNNV prior to infection with RGNNV, may be less than in the group that was not administered SJNNV. In this situation, prior administration of SJNNV may be said to have reduced the symptoms and/or mortality caused by or associated with RGNNV. Reductions in properties like symptoms and mortality, due to SJNNV administration, may indicate protection against disease associated with or caused by RGNNV.

Herein, "administering" or "inoculating," generally as referred to viruses and their interaction with fish and/or cells, means that virus is intentionally given to, applied to or introduced into, the fish or cells, such that the viruses can infect, or at least adsorb to, cells in the fish or cells cultured in vitro. One method of administering or inoculating virus is by injection of virus into the body of a fish.

Herein, "exposure to" or "exposed to," generally refers to a situation where an animal (e.g., a fish) is in proximity to an infectious agent (e.g., a virus) such that there is a possibility that or opportunity for the virus to infect cells of the animal.

Herein, "subsequently administering" or "subsequently inoculating," generally refers to a situation where a virus is administered to a fish at a time after some other event has occurred. In one example, one virus (e.g., RGNNV) is administered to a fish at a point in time after a different virus (e.g., SJNNV) has been administered to the fish. In this situation, RGNNV may be said to have been "subsequently administered" in relation to the earlier administration of SJNNV.

Herein, "infection," refers to the process whereby a virus interacts with a host cell and is multiplied, or at least has the opportunity to multiply, within the host cell such that additional viruses are produced. It is possible for the infection process to be interrupted or blocked at various stages. When the infection process is interrupted or blocked, production of additional viruses may be inhibited or reduced.

Herein, "coinfection," generally refers to the process whereby different viruses (e.g., a SJNNV and a RGNNV) interact with the same host cell at approximately the same time or simultaneously. In one example, coinfection of a cell by two different viruses results in coexistence of genomes from both viruses inside of a host cell.

Herein, "superinfection," refers to the situation where two viruses interact with the same host cell at approximately different times. For example, in the instance where cells are exposed to SJNNV such that an infection of cells with SJNNV may be initiated and, at some later time, the cells are exposed to RGNNV such that an infection with RGNNV may be initiated, SJNNV may be said to be the "infecting" virus and RGNNV may be said to be the "superinfecting" virus. Superinfection, therefore, generally refers to infection of cells with a virus where the cells have previously been infected with a virus. An infecting virus may be said to have infected cells prior to a superinfecting virus. A superinfecting virus may be said to have infected cells subsequent to an infecting virus.

Herein, "replication," generally refers to the process where viral genomes are reproduced in the interior of a host cell. Generally, replication includes a subset of the events that occur during infection.

Herein, "reassortant," generally refers to a virus with a multipartite genome (e.g., a genome in multiple segments) where the origin of at least two genome segments can be attributed to viruses that are not the same. For example, betanodaviruses are known that appear to have one genome RNA molecule that originated from SJNNV and a second genome RNA molecule that originated from RGNNV.

Herein, "transcriptional expression," refers to synthesis of RNA from a DNA copy of a gene. In one example, steady-state levels of RNA encoded by specific genes within cells may be measured and used to infer regulation of expression of the gene at the level of transcription. In one example, levels of RNA encoded by a gene is measured in different populations of cells, and differences in the RNA levels is attributed to a change in the rate of transcription of that gene.

Disclosed herein are interactions between, and the effects of interactions between, betanodaviruses in infection of fish, or cells in vitro. The betanodaviruses described are generally viruses of the SJNNV species and viruses of the RGNNV species. In one example, infection of fish with an SJNNV can reduce or diminish disease, symptoms of disease, effects of disease, and the like, of a superinfecting RGNNV, as compared to disease/symptoms/effects of an RGNNV in absence of a prior SJNNV infection.

The effect of infecting SJNNV on superinfecting RGNNV may be seen in a variety of species of fish. Generally, the fish include any species that can be infected by SJNNV and RGNNV. Some examples include European sea bass (*Dicentrarchus labrax*), Senegalese sole (*Solea senegalensis*), gilt-head sea bream (*Sparus aurata*), red-banded seabream (*Pagrus auriga*), common seabream (*Pagrus pagrus*) and white seabream (*Diploidus sargus*).

Generally, the SJNNV may be an SJNNV that can infect a fish species that RGNNV can also infect. In one example, the infecting SJNNV may cause fewer or less severe symptoms than does a superinfecting RGNNV. In one example, SJNNV may be the SJ93Nag strain or isolate (Iwamoto et al, 2001). Other SJNNV isolates may include SJOri, SJ91Nag, SJ92Nag, SJ94Nag and RS95Hir.

"Serologically reacts with antiserum" may be tested by methods well known in the art. Examples of tests for detecting serological cross reaction are ELISA, hemagglutination inhibition (HI), serum neutralization (SN) assay, cross neutralization test and virus neutralization test. A preferred example is the cross neutralization test. See Mori et al., 2003, p21 for the methodology used to test serological cross reaction with antiserum for nodavirus isolates.

SJNNV may be purified from diseased larvae of Striped jack fish and the RNA extracted by methods well known in the art, for example as described by Nishizawa et al 1995, p1564.

Identity of the RNA virus as belonging within the SJNNV genotype according to the invention may be established by comparison with the variable region of the SJNag93 coat protein gene sequence from nucleotides 604 to 1030 of RNA2 (SEQ ID NO: 4), or at the amino acid level aa 204 to 331 of SEQ ID NO: 5, preferably 223 to 331, more preferably 235 to 315, as described by Nishizawa et al., 1997, particularly on page 1635, and Nishizawa et al., 1995 and Skiliris et al., page 64.

Infectious RNA transcripts for SJNNV may alternatively be made by methods well known in the art, based on the known sequences of SJNNV (See seq ID No. 1-5). This has been descried in detail in Iwamoto et al 2001, p2654-2656.

Generally, the RGNNV may infect a fish species that SJNNV can also infect. In one example, RGNNV causes symptoms and/or disease in the infected fish. In one example, RGNNV can cause mortality in the infected fish. An example RGNNV strain or isolate is ERV378/102-5/04 (Lopez-Jimena et al., 2011).

The betanodaviruses may be propagated by a variety of methods. For example, the viruses may be grown in cultured cells. A variety of cultured cells may be used. Some example cell lines include the E-11 cell line (ECACC, No. 01110916; Iwamoto et al., 2000), SAF-1 cells (ECACC, No. 00122301; Aquaculture 150:143-153, 1997) and SSN-1 cells (J. Gen. Virol. 77, 2067-2071, 1996). Techniques for propagating the viruses are well known in the field.

Administration of viruses, including SJNNV, to fish may be performed using a variety of techniques. For example, SJNNV may be administered to larvae and/or juveniles of a fish species. SJNNV may be administered to adult or mature fish. In one example, fish are between about 2.5 g and 10 g in weight. Routes of administration of SJNNV may vary. Examples include intramuscular injection, intraperitoneal injection, orally in feed, immersion of fish in a bath containing the virus, and others.

Generally, the amount of SJNNV administered to fish is an amount that reduces symptoms, including mortality, that may be caused by RGNNV. The "amount" of virus may be determined by a variety of techniques. Generally, assays that measure infectious activity of viruses may be used. In one example, infectious virus may be measured by determining $TCID_{50}$. Other methods may measure plaque-forming units. Additional methods may be used. The amount of SJNNV administered may be $10^2$, $10^3$, $10^5$, $10^6$, $10^7$, or more $TCID_{50}$/fish. In one example, the amount of SJNNV administered to fish is at least about $1\times10^4$ $TCID_{50}$/fish. In one example, the amount of SJNNV administered to fish is between about $1\times10^4$ and $1.5\times10^4$ $TCID_{50}$/fish. Example volumes infected into the fish may be 10, 20, 50, 100, 150, 200, 250 or 500 μl. In one example, the volume is between about 10 and 200 μl. In another example, 50 or 100 μl is injected.

Formulation of the viruses for administration to fish may be performed using a variety of methods. Generally, the formulation will preserve the infectivity of the viruses until the time the viruses are administered to fish. In one example, viruses may be formulated in a biological buffer.

The effect SJNNV has on reducing symptoms in fish that are caused by RGNNV generally may be long lasting. For example, fish administered SJNNV may display reduced symptoms due to subsequent RGNNV infection for various times after administering SJNNV. In various examples, fish administered SJNNV may have reduced symptoms due to subsequent RGNNV infection, as compared to fish not administered SJNNV, for 6, 5, 4, 3, 2 or 1 week(s) after administration of SJNNV. The reduced symptoms may have durations of 6, 5, 4, 3, 2 or 1 day(s) after administration after SJNNV. The reduced symptoms may have durations of 96, 72, 48, 24, 12 or 6 hours after administration of SJNNV.

No mechanism of action for the effect of SJNNV on disease and/or mortality associated with RGNNV is relied upon or offered. It is merely disclosed that example results indicate that infection of fish and/or cells of or from fish may result in or be associated with changes in expression of one or more genes known to be regulated by interferon. In one example, infection of fish with SJNNV is associated with increased levels of steady-state RNA from one or more interferon-inducible gene. In one example, the interferon-inducible gene may be Mx. In one example, SJNNV is associated with increased transcription from the interferon-inducible genes.

In one example, infection of cells with RGNNV prior to, or simultaneously with, SJVVN may result in inhibition of replication of SJNNV in the cells. SJNNV superinfection of cells infected with RGNNV may cause inhibition of genome replication of SJNNV. RGNNV and SJNNV coinfection of cells may cause inhibition of genome replication of SJNNV.

In one example, infection of cells with SJNNV prior to, or simultaneously with, RGNNV may result in stimulation of replication of RGNNV in cells. RGNNV superinfection of cells infected with SJNNV may cause stimulation of genome replication of RGNNV. SJNNV and RGNNV coinfection of cells may cause stimulation of genome replication of RGNNV.

EXAMPLES

The examples are for the purpose of illustrating an example and are not to be construed as illustrating limitations.

Example 1—Betanodaviruses, Cell Line and Virus Growth

Viral isolates ERV378/102-5/04 (RGNNV genotype; Lopez-Jimena et al, 2011), SpDI-IAusc1688.08 (RGNNV genotype; Olveira et al, 2009), SJ93Nag (SJNNV genotype, Iwamoto et al, 2001), and SpSs-IAusc160.03 (reassortant with RGNNV-type RNA1 and SJNNV-type RNA2; Olveira et al, 2009) were grown at 25° C. on the E-11 cell line (European Collection of Cell Cultures, UK, Cat. No. 01110916) (Iwamoto et al., 2000) according to Lopez-Jimena et al., 2011. Cells were grown at 25° C. in Leibovitz (L-15) medium (Invitrogen) supplemented with 1% penicillin-streptomycin (Invitrogen) and 5% fetal bovine serum, until semi-confluent, before virus inoculation. Virus titers were determined by using the highest dilution causing cytopathic effect in 50% of the inoculated cultures ($TCID_{50}$) as described (Tissue Culture: Methods and Applications; Kruse and Patterson, eds.; pp. 527-532, Academic Press, New York, 1973).

Example 2—Sea Bass

European sea bass (*Dicentrarchus labrax*) were maintained at between 21-25° C. Sea bass of the indicated weights were inoculated with viruses by intramuscular (i.m.) injection (0.1 ml of L-15 medium was used as control inoculum for controls). In other studies, sea bass were inoculated by immersion of fish in a bath that contained virus (L-15 medium used as inoculum for controls).

Example 3—Sea Bass Mortality Caused by Some RGNNV Strains

Figure 2:
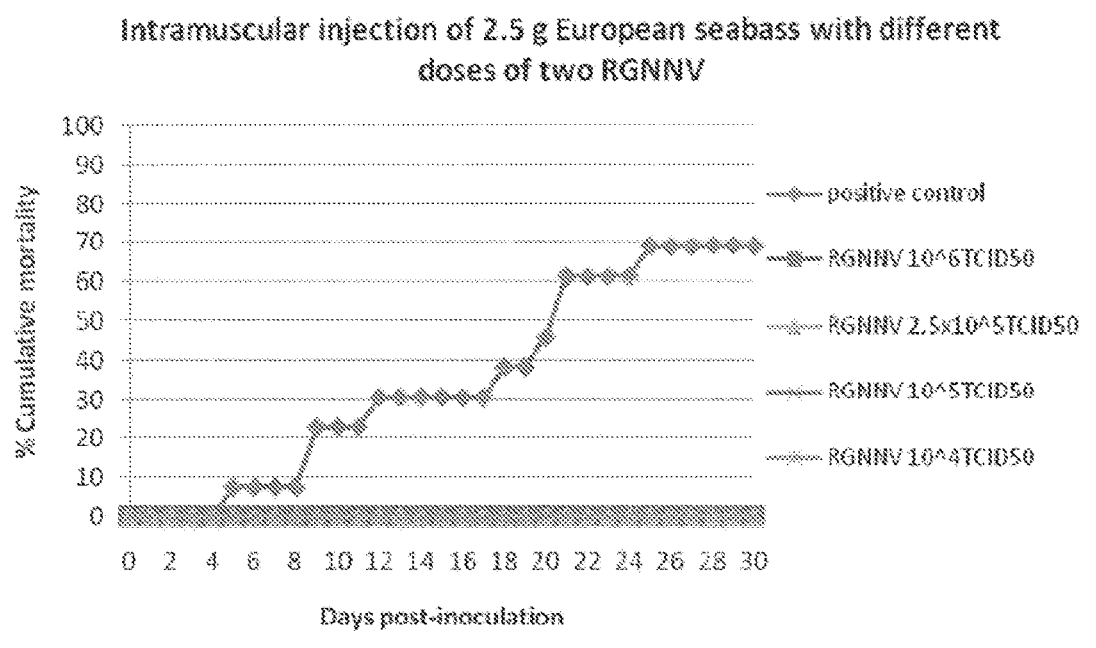

European sea bass of 2.5 g average weight were injected i.m. with $1.0 \times 10^6$, $2.5 \times 10^5$ $1.0 \times 10^5$ or $1.0 \times 10^4$ $TCID_{50}$/fish of the viral isolate SpDI-IAusc1688.08 (RGNNV genotype). Fish were similarly injected with $2.5 \times 10^5$ $TCID_{50}$/fish of the viral isolate ERV378/102-5/04 RGNNV genotype (listed as positive control in FIG. 2). The ERV378/102-5/04 isolate caused a cumulative mortality rate of 69% in this study.

In another experiment (Lopez-Jimena et al., 2011) it was shown that, in juvenile European sea bass (mean weight 10±0.3 g; n=100) that were challenged with $10^6$ $TCID_{50}$ of the ERV378/102-5/04 RGNNV isolate by i.m. injection, cumulative fish mortality was 37%. Analyses of tissue homogenates (brain and eyes) from dead fish by cell culture inoculation demonstrated the presence of RGNNV in all the samples analyzed. Identity of the virus was subsequently confirmed using RT-PCR.

Example 4—Different *Betanodavirus* Genotypes and Fish Mortality

Figure 1:
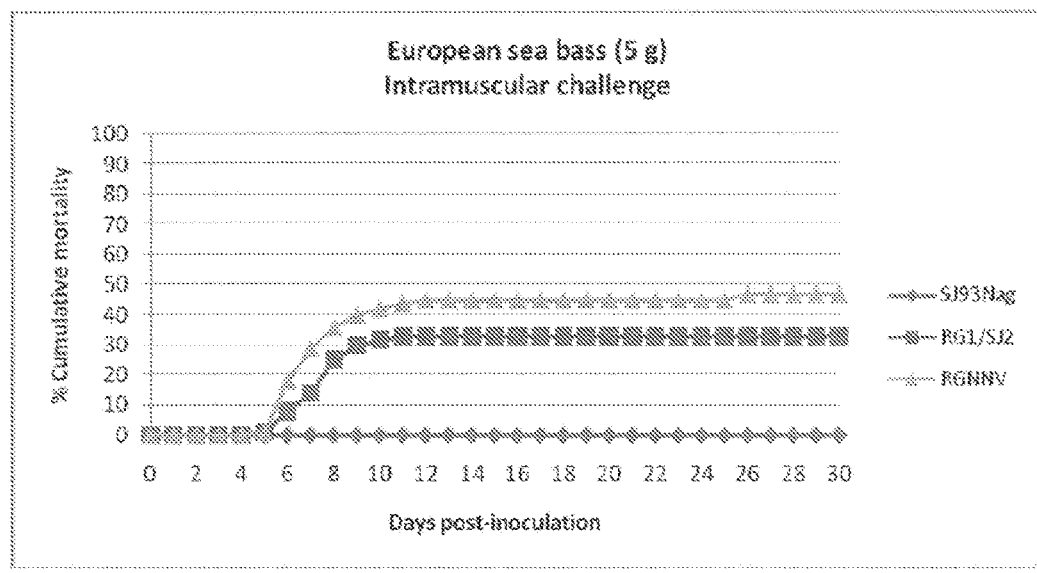
FIG. 1 illustrates example data from a study where different *betanodavirus* genotypes were administered to 5 g juvenile sea bass and fish mortality was followed.

Sea bass 5 g weight were i.m. challenged with the following VNN isolates: SJ93Nag (SJNNV genotype), isolate ERV378/102-5/04 (RGNNV), and SpSs-IAusc160.03 (reassortant RGNNV RNA1 and SJNNV RNA2). A volume of 0.1 ml L-15 medium was injected in the control group, whereas the dose of 2.5×105 TCID50/fish of the different virus was used. Temperature was measured daily and maintained between 22-25° C. approximately. Typical symptoms of VNN and mortality were only recorded in fish inoculated with the RGNNV (47% cumulative mortality), and reassortant (33% cumulative mortality). No mortality was recorded from the SJ93Nag or the control group (FIG. 1).

Example 5—Determination of the Anti-VNNV Antibodies in Fish Survivors

Sera from 5 fish survivors from Example 4 were pooled and three pools were screened in order to detect specific anti-*betanodavirus* antibodies by ELISA. ELISA plates were coated with either SJ93Nag (SJNNV genotype), SpSs-IAusc160.03 (reassortant RGNNV RNA1/SJNNV RNA2) or RGNNV (Lopez-Jimena et al., 2011) and pooled sera (1/32 dilution) were analysed in triplicate. The optical density (OD) was determined at 450 nm. The OD mean of the negative control wells (PBS instead of fish serum) (three times repetitive) was the cut-off threshold considered.

Table 1 shows the mean OD values and standard deviation (SD) of the three replicates. The cut-off threshold value was 0.305.

TABLE 1

Mean OD values and standard deviation (SD) of specific anti-VNN antibody detection using ELISA

|  | Sera 2 g seabass CONTROL | Sera 2 g seabass CONTROL 30 dpi | Sera 2 g seabass CONTROL 0 dpi | Sera 2 g seabass ANTIGEN |
|---|---|---|---|---|
| MEAN | 0.026472222 | 0.041805556 | 0.037916667 | SJ93Nag |
| SD | 0.005738112 | 0.009912581 | 0.013670731 |  |
| MEAN | 0.026583333 | 0.040805556 | 0.04625 | RG RNA1/ SJ RNA2 |
| SD | 0.006437736 | 0.008921468 | 0.004714045 |  |
| MEAN | 0.039361111 | 0.052694444 | 0.061583333 | RGNNV |
| SD | 0.005853141 | 0.010286633 | 0.017913372 |  |

|  | Sera 5 g seabass SJ93Nag | Sera 5 g seabass RG RNA1/ SJ RNA2 | Sera 5 g seabass RGNNV | ANTIGEN |
|---|---|---|---|---|
| MEAN | 0.83281944 | 0.871597222 | 0.83670833 | SJ93Nag |
| SD | 0.07542865 | 0.085379111 | 0.07819065 |  |
| MEAN | 0.82926389 | 0.86881944 | 0.84126389 | RG RNA1/ SJ RNA2 |
| SD | 0.10151373 | 0.067798995 | 0.11232756 |  |
| MEAN | 0.05815278 | 0.126152778 | 0.42470833 | RGNNV |
| SD | 0.02060295 | 0.079490973 | 0.09031488 |  |

High levels of viral genome and infective viral particles were recorded in the brain of survivor fish inoculated with the SJNNV isolate, although there was no mortality or clinical signs. Specific antibody response, measured by indirect ELISA, was only observed in the VNN-innoculated groups, with titres of 1/1024, 1/4096 and 1/8192 for RGNNV, SJNNV and the reassortant inoculated fish respectively.

Example 6—Effect of Sea Bass Size on Mortality

Figure 3:
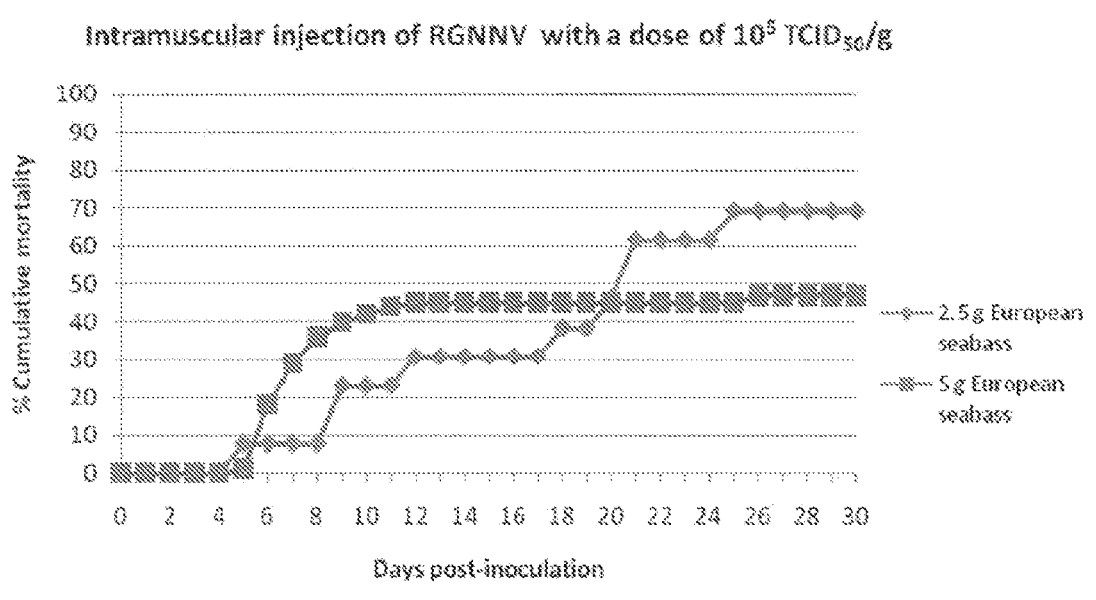

European sea bass of 2.5 g average weight were injected i.m. with $2.5 \times 10^5$ $TCID_{50}$/fish of the viral isolate ERV378/102-5/04 (RGNNV genotype). Fish mortality was recorded daily. The ERV378/102-5/04 isolate of RGNNV caused a cumulative mortality rate of 69%. As mentioned in Example 4, the same inoculation to sea bass of average weight 5 g resulted in 47% cumulative mortality. The data for the 2.5 and 5 g fish are shown in FIG. 3. In third trial, inoculation of $10^6$ $TCID_{50}$ of the same virus to sea bass of average weight 10 g resulted in 37% mortality. Fish size is therefore inversely related with mortality rate for infection with RGNNV genotype.

Example 7—Superinfection Experiments in Fish

Studies were performed to monitor the course of disease in sea bass infected with RGNNV, when the sea bass had previously been infected with SJNNV.

Juvenile European sea bass (average weight 10-15 g) were distributed into four separate tanks of 600 L:

Non-infected control group (n=150): i.m. injected with L-15 medium (0.1 ml) at time 0 and again 24 hours later;
1) Non-infected control group (n=150): i.m. injected with 0.1 ml of L-15 medium at time 0 and 25 hours later;
2) SJNNV-infected control group (n=150): i.m. injected with $1.5 \times 10^6$ $TCID_{50}$ SJNNV (isolate SJ93Nag) at time 0 and with L-15 medium (0.1 ml) 24 hours later;
3) RGNNV-infected control group (n=150): i.m. injected with L-15 medium (0.1 ml) at time 0 and with $1.5 \times 10^6$ $TCID_{50}$ RGNNV (isolate ERV378/102-5/04) 24 hours later;
4) Superinfected group (n=150): i.m. injected with $1.5 \times 10^6$ $TCID_{50}$ SJNNV (isolate SJ93Nag) at time 0 and then with $1.5 \times 10^6$ $TCID_{50}$ RGNNV (isolate ERV378/102-5/04) 24 hours later.

From each experimental group, 50 fish were kept separately for use to determine cumulative mortality. The remaining 100 fish were used for sampling (see data in Examples 8-10). Water temperature was maintained between 22 and 24° C. over the course of the trial. Mortality was recorded daily and dead fish were frozen at −80° C. for use in later virological examinations.

Figure 4:
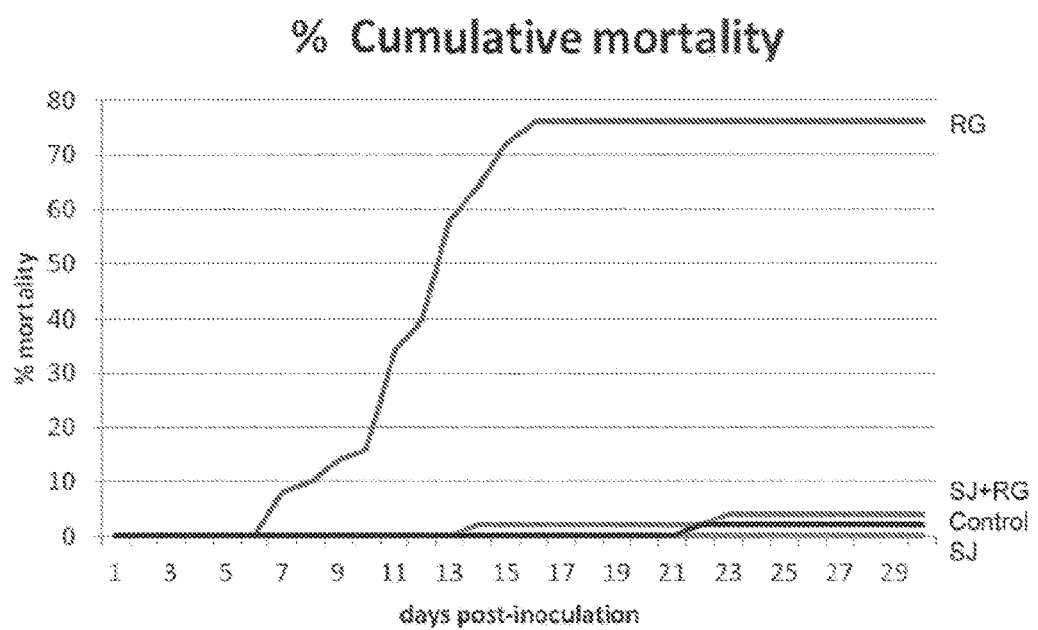
FIG. 4 illustrates example data from a study where an RGNNV strain was administered to sea bass that had already been administered SJNNV (e.g., RGNNV superinfection of fish infected with SJNNV). Fish mortality was followed.

For the SJNNV-infected control group (Group 2), as well as in the non-infected control group (Group 1), no mortality was observed (FIG. 4).

For the RGNNV-inoculated control group (Group 3), mortality was first detected at about 6 days post infection. Mortality stabilized at about 76%, 15 days post infection.

In the superinfected group (Group 4), although fish exhibited dark coloration and abnormal swimming behavior, only 2 animals died (4% cumulative mortality). In this group, SJNNV infection dramatically reduced the mortality seen when RGNNV infected fish without prior SNJJV infection (Group 3).

Example 8—Virus From Dead RGNNV-Infected Fish in the Superinfection Experiments

Dead fish from the RGNNV-infected control group (Group 3), from the experiment described in Example 7, were assayed for the presence of virus. Brain and eye tissue from fish found dead on day 6 and on day 12 post infection, were pooled, and homogenized in 20% (w/v) L-15 medium supplemented with 1% penicillin-streptomycin and 2% fetal bovine serum. Homogenates were treated with 10% penicillin-streptomycin at 4° C. overnight. Homogenates were then centrifuged twice at 7,500×g at 4° C. for 15 min, and 100 μl of the supernatants were used for virus titrations on E-11 cells to determine $TCID_{50}$. The data are shown in Table 2, below.

TABLE 2

Viral titers from dead fish from the RGNNV-infected control group

| Days post infection fish found dead | Viral titer ($TCID_{50}$/g) |
|---|---|
| 6 | $1.6 \times 10^9$ |
| 12 | $1.6 \times 10^8$ |

These data indicate that the virus could be isolated from the dead fish.

Example 9—Quantification of Viral Genomes from SJNNV-Infected, RGNNV-Superinfected Fish in Superinfection Experiments Quantification of viral genomes in fish from the superinfected group (Group 4), from the experiment described in Example 7, was performed. Nine live fish were randomly collected from Group 4 at 12 hours, 3 days, and 7 days after the RGNNV superinfection. Fish were killed by an overdose of anaesthetic (MS-222, Sigma), and the brain and eyes from the 3 fish at each time point were pooled together, immediately frozen in liquid nitrogen, and stored at −80° C. until used.

The pooled organs were homogenized in L-15 medium (20% w/v) supplemented with 1% penicillin-streptomycin and 2% FBS. Homogenates were centrifugated twice at 7,500×g at 4° C. for 15 min. Volumes of 200 μl of the three clarified homogenates, at every sampling time, were used for total RNA extraction.

RNA extraction was performed using Trizol® (Invitrogen). RNA concentration obtained was determined at 260 nm using the ND-1000 system (NanoDrop Thermo Scientific). RNA was stored at −80° C. until used.

Synthesis of cDNA from the RNA was performed using the Transcriptor First-Strand cDNA Synthesis kit (Roche). The reaction was carried out with 1 μg of total RNA. The cDNA concentration was determined at 260 nm using the ND-1000 system. cDNA was stored at −20° C. until used.

Viral genomes were quantified using SYBR Green I-based absolute real-time PCR (qPCR) protocols detecting, separately, the RNA2 segments of the RGNNV and SJNNV genotypes. Specifically, RGNNV RNA2 was quantified using a procedure already described (Lopez-Jimena et al., 2011). SJNNV RNA2 segment was quantified using the primers SJ-RNA2-F (5'-GACACCACCGCTCCAATTAC-TAC-3', nucleotides 665-687) (SEQ ID NO. 6) and SJ-RNA2-R (5'-ACGAAATCCAGTGTAACCGTTGT-3', nucleotides 739-717) (SEQ ID NO. 7), that amplify a 75-bp fragment within the T4 region (GenBank accession number D30814), using the PCR conditions already described (Lopez-Jimena et al., 2011).

Significant differences between the number of copies of each viral genome segment at different times p.i. were calculated by one-way ANOVA, followed by Fisher's Least Significant Difference (LSD) Test. Statistical analysis was performed using IBM SPSS Statistics software. Values of $p<0.05$ were considered significant.

Figure 5:
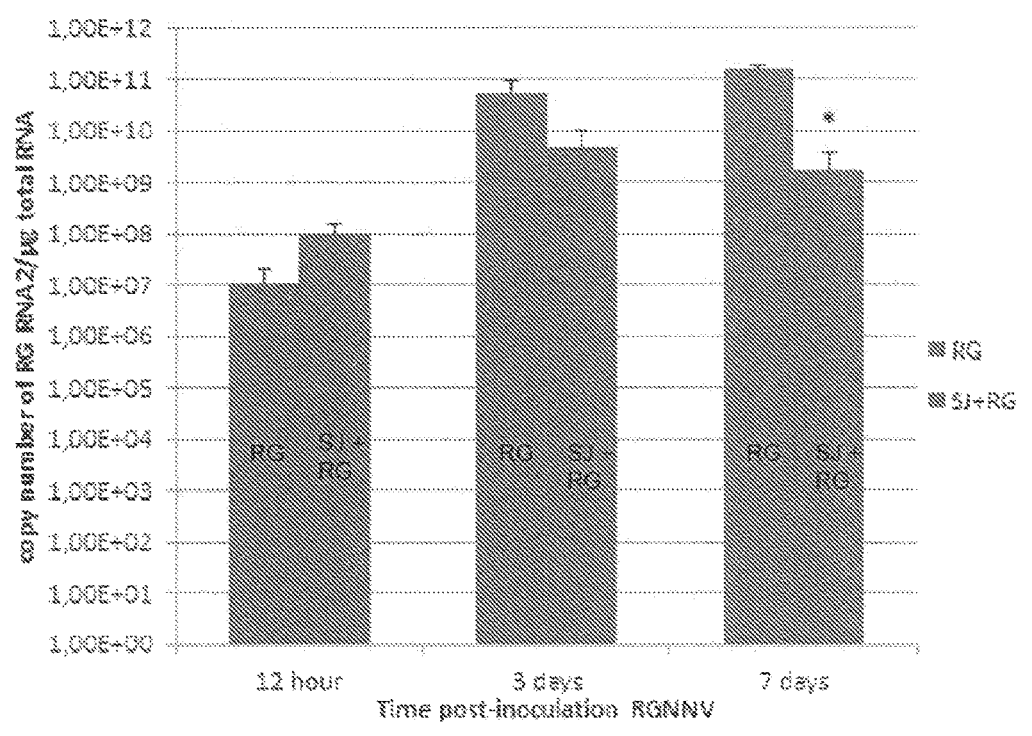

For quantification of RGNNV genomes, the data (FIG. 5) showed a significant decrease in RGNNV replication in the Superinfected group (Group 4) at 7 days after superinfection with RGNNV (8 days after infection with SJNNV) as compared with the RGNNV-inoculated control group (Group 3) (FIG. 5).

Figure 6:
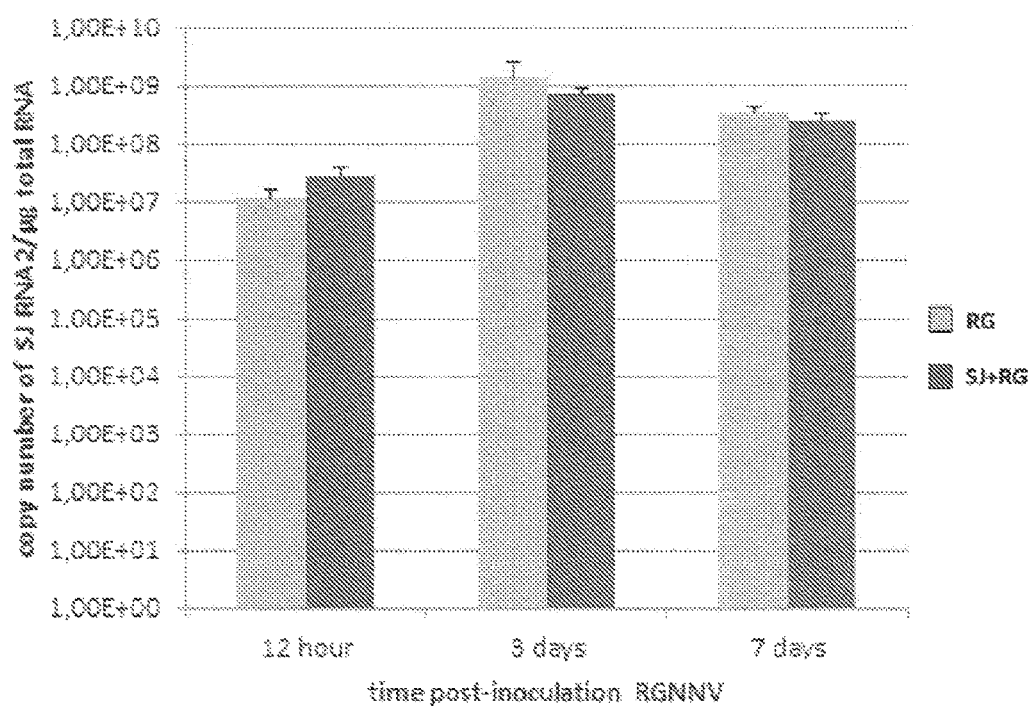
FIG. 6 illustrates example data from a study where SJNNV genome RNA was quantified at various times after fish infected with SJNNV had been superinfected with RGNNV. First column at each time point is the SJ control group (group 2) and second column at each time point is the SJ/RG group (group 4).

In contrast, no significant differences were observed when SJNNV replication in the Superinfected group (Group 4) was compared to the SJNNV-infected control group (Group 2) (FIG. 6).

Example 10—Interferon (IFN)-Inducible Gene Expression in Superinfection Experiments Fish from the experiments described in Example 7 were tested for transcriptional expression of the IFN-inducible gene, Mx, using real time, RT-qPCR. The data showed no transcriptional expression of Mx in fish from the RGNNV-infected control group (Group 3) from 0 to 48 hours post infection. In contrast, Mx transcriptional expression was increased in fish from the SJNNV-infected control group (Group 2) and from the Superinfected group (Group 4). These data indicate that infection of fish by SJNNV may induce the IFN-inducible gene, Mx, while RGNNV does not. These results suggest that the induction of the IFN mediated system by the previous infection with SJNNV could be responsible for the decrease in the mortality recorded in the superinfected group, protecting sea bass from the effects of posterior infection with RGNNV.

Example 11—Superinfection Experiments in Cultured Cells

Studies were performed to investigate the effects of coexistence of SJNNV and RGNNV on the replication and multiplication of each virus. Viral genome copy number in infected cells, and production of infective virus particles produced by infected cells was determined. E-11 cells were grown in 24-wells plates. Second-passage cell monolayers, in duplicate, were infected at a multiplicity of infection of 0.1 at 25° C., a temperature optimum for multiplication of both SJNNV and RGNNV. The experimental groups were as shown in Table 3, below. In each experimental group, non-inoculated E-11 cells were included as a control.

TABLE 3

Experimental groups and sampling times analyzed

| Group | Virus genotype(s) inoculated | Hours postinfection samples taken |
|---|---|---|
| 1 | SJNNV-infected control group | $0^a$, 12, 24, 48, 72, 96 |
| 2 | RGNNV-infected control group | $0^a$, 12, 24, 48, 72, 96 |
| 3 | SJNNV + RGNNV coinfection group | $0^a$, 12, 24, 48, 72, 96 |
| 4 | SJNNV → 24 h → RGNNV superinfection group | $0^{a,b}$, $12^b$, $24^b$, $24^c$, $48^c$, $72^c$ (SJNNV) $0^{a,c}$, $12^c$, $24^c$, $48^c$, $72^c$, $96^c$ (RGNNV) |
| 5 | RGNNV → 24 h → SJNNV superinfection group | $0^{a,d}$, $12^d$, $24^d$, $24^e$, $48^e$, $72^e$ (RGNNV) $0^{a,e}$, $12^e$, $24^e$, $48^e$, $72^e$, $96^e$ (SJNNV) |

$^a$Samples taken after 1 hour virus adsorption
$^b$Times after SJNNV infection
$^c$Times after RGNNV superinfection
$^d$Times after RGNNV infection
$^e$Times after SJNNV superinfection At the times indicated in Table 3, both cells and supernatants were collected from 2 wells of each experimental group. Negative controls were collected at the end of the experiment. Total RNA was extracted from the cells using Trizol®, as described in Example 9. cDNA was synthesized using the SuperScript™ II First-Strand Synthesis System for RT-PCR (Invitrogen), following manufacturer's instructions and adding random hexamers (50 ng) and 1 μg of total RNA in each reaction. Viral genomes were quantified using SYBR Green I-based absolute real-time PCR (qPCR), and the data were analyzed, also as described in Example 9.

To determine viral titers, several cell-free supernatants were titrated to determine $TCID_{50}$ (Example 1). In groups 3 to 5, neutralization assays were performed before viral titration using the following polyclonal antibodies (1/100 dilution in L-15 medium, supplemented with 1% penicillin-streptomycin): (i) anti-NNV ab26812 (Abcam), that neutralizes the RGNNV genotype, and (ii) an anti-SJNNV antibody developed in rabbit (Dr T. Nakai, University of Hiroshima, Japan), that neutralizes SJNNV.

Figure 7:
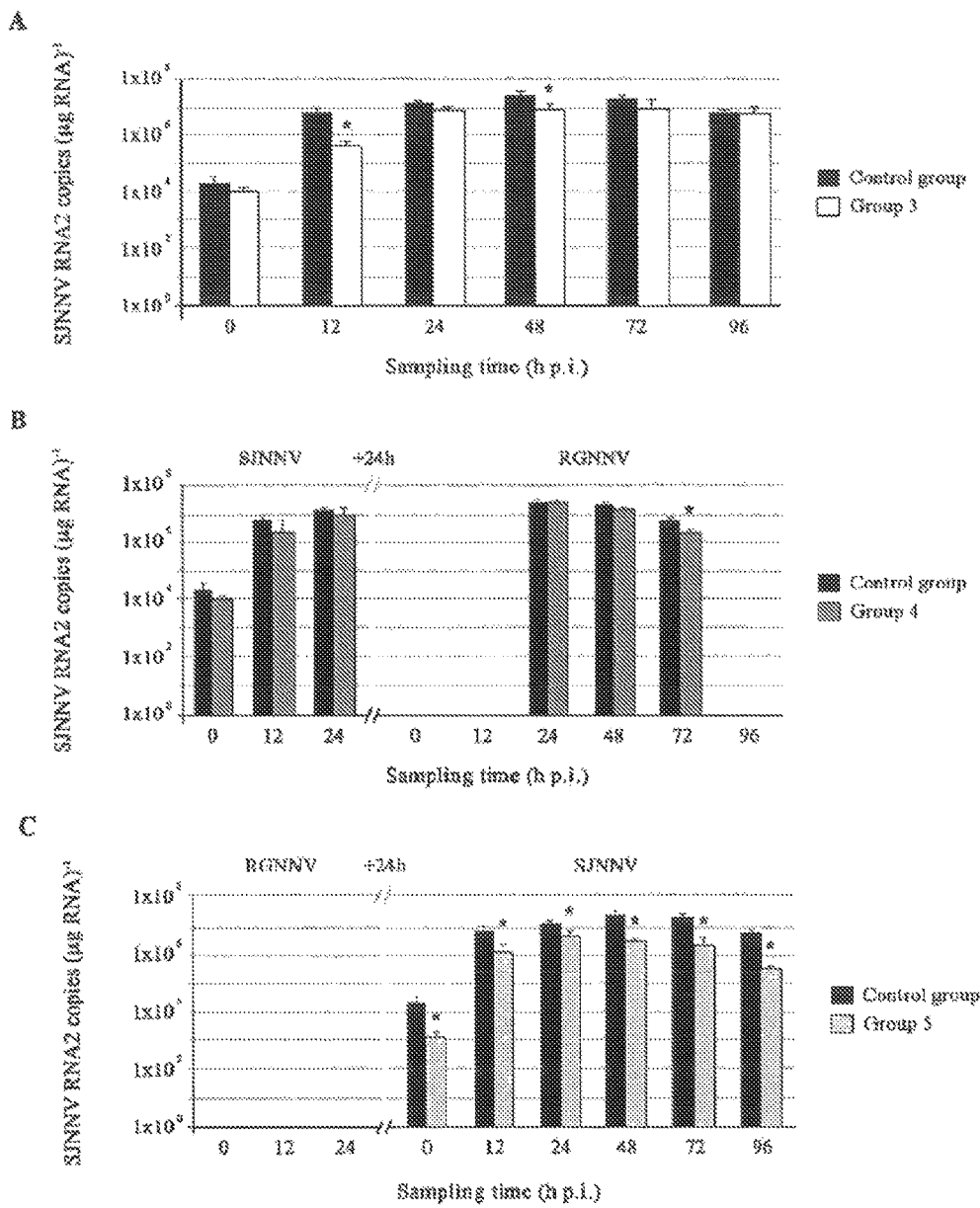
FIG. 7 illustrates example data from studies where SJNNV genome RNA was quantified at various times after: (A) cells were coinfected with SJNNV and RGNNV, (B)

FIG. 7 shows measurements of SJNNV RNA 2 copy number in infected cells. FIG. 7A shows SJNNV copy number in the SJNNV+RGNNV coinfection group (Group 3), compared to SJNNV copy number in the SJNNV-infected control group (Group 1). FIG. 7B shows SJNNV copy number in the SJNNV infection, 24 hours later RGNNV coinfection group (Group 4), compared to copy number in the SJNNV-infected control group (Group 1). FIG. 7C shows SJNNV copy number in the RGNNV infection, 24 hours later SJNNV superinfection group (Group 5), compared to the copy number in the SJNNV-infected control group (Group 1). Bars show the standard deviation of two different samples. Statistically significant changes ($p<0.01$) are represented by an asterisk.

FIG. 8 shows measurements of RGNNV RNA 2 copy number in infected cells. FIG. 8A shows RGNNV copy number in the SJNNV+RGNNV coinfection group (Group 3), compared to RGNNV copy number in the RGNNV-infected control group (Group 2). FIG. 8B shows RGNNV copy number in the SJNNV infection, 24 hours later RGNNV coinfection group (Group 4), compared to copy number in the RGNNV-infected control group (Group 2). FIG. 8C shows RGNNV copy number in the RGNNV infection, 24 hours later SJNNV superinfection group (Group 5), compared to the copy number in the RGNNV-infected control group (Group 2). Bars show the standard deviation of two different samples. Statistically significant changes (p<0.01) are represented by an asterisk.

The data from these experiments indicated that, in cells infected with SJNNV and RGNNV: i) SJNNV genome replication was partially inhibited in the presence of RGNNV; ii) RGNNV genome replication was stimulated in the presence of SJNNV, and iii) these effects on genome replication did not correlate with production of infectious virus.

The data indicating inhibition of SJNNV replication by RGNNV is described as follows. In the coinfection group (Group 3), the data (FIG. 7A) showed a decrease in SJNNV genome copy number, as compared to the control group (Group 1), at the 12 and 48 hour time points. This was more apparent in the experiment where RGNNV-infected cells were superinfected 24 hours later with SJNNV (Group 5). In that experiment, the data (FIG. 7C) showed a decrease in SJNNV genome copy number, as compared to the control group (Group 1), at the 0, 12, 24, 48, 72 and 96 hour time points. These decreases in SJNNV genome copy number were not clearly correlated with titers of SJNNV virus produced by the cells.

le;.3qThe data indicating stimulation of RGNNV replication by SJNNV is described as follows. In the coinfection group (Group 3), the data (FIG. 8A) showed an increase in RGNNV genome copy number, as compared to the control group (Group 2), at the 24, 48 and 72 hour time points. This was more apparent in the experiment where SJNNV-infected cells were superinfected 24 hours later with RGNNV (Group 4). In that experiment, the data (FIG. 8B) showed an increase in RGNNV genome copy number, as compared to the control group (Group 2), at the 0, 12, 24 and 48 hour time points. However, at 96 hours, RGNNV genome copy number was decreased as compared to the control group. The increases in RGNNV genome copy number were not clearly correlated with titers of RGNNV virus produced by the cells.

We have also found that infection of cells with SJNNV, prior to or approximately simultaneous with RGNNV infection, at least initially stimulates replication of RGNNV RNA in the cells, as compared to replication of RGNNV in cells that do not contain SJNNV. This effect on replication may not correlate with infectious virus produced by the infected cells.

We have also found that infection of cells with RGNNV, prior to or approximately simultaneous with SJNNV infection, partially inhibits replication of SJNNV RNA in the cells, as compared to replication of SJNNV in cells that do not contain RGNNV. This effect on replication may not correlate with infectious virus produced by the infected cells.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the disclosure is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

REFERENCES

Iwamoto T, Nakai T, Mori K, Arimoto M, Furusawa I "Cloning of the fish cell line SSN-1 for piscine nodaviruses". Dis Aquat Organ. 2000 November 14; 43(2):81-9.
Iwamoto et al "Establishment of an infectious RNA transcription system for the Striped Jack nervous necrosis virus, the type species of the betanodaviruses" Journal. of General Virology (2001), 82, 2653-2662
Lopez-Jimena B, Alonso Mdel C, Thompson K D, Adams A, Infante C, Castro D, Borrego J J, "Tissue distribution of Red Spotted Grouper Nervous Necrosis Virus (RGNNV) genome in experimentally infected juvenile European seabass (*Dicentrarchus labrax*)." Vet Microbiol. 2011 December 29; 154(1-2):86-95
Mori, K, Mangyoku, T, Iwamoto, T, Arimoto, M, Tanaka, Si, Nakai, T "Serological relationships among genotypic variants of *betanodavirus*" Diseases of Aquatic Organisms Vol. 57 no.1-2 page.19-26 (20031203)
Nishizawa T, Mori K, Furuhashi M, Nakai T, Furusawa I, Muroga K. "Comparison of the coat protein genes of five fish nodaviruses, the causative agents of viral nervous necrosis in marine fish" J Gen Virol. 1995 July; 76 (Pt 7):1563-9.
NISHIZAWA, M. FURUHASHI, T. NAGAI, T. NAKAI, AND K. MUROGA "Genomic Classification of Fish Nodaviruses by Molecular Phylogenetic Analysis of the Coat Protein Gene" APPLIED AND ENVIRONMENTAL MICROBIOLOGY, April 1997, p. 1633-1636
Olveira J G, Souto S, Dopazo C P, Thiéry R, Barja J L, Bandin I. "Comparative analysis of both genomic segments of betanodaviruses isolated from epizootic outbreaks in farmed fish species provides evidence for genetic reassortment." J Gen Virol. 2009 December; 90(Pt 12):2940-51
Skliris G P, Krondiris J V, Sideris D C, Shinn A P, Starkey W G, Richards R H. "Phylogenetic and antigenic characterization of new fish nodavirus isolates from Europe and Asia." Virus Res. 2001 May; 75(1):59-67
Virus Taxonomy: Ninth Report of the International Committee on Taxonomy of Viruses, Elsevier 2012, Chapter Nodaviridae (Betanovirus), p 1061-1067

The invention claimed is:

1. Vaccine comprising striped jack nervous necrosis virus (SJNNV), wherein the vaccine protects a fish against red-spotted grouper nervous necrosis virus (RGNNV) infection;
   wherein the fish is selected from the group consisting of European sea bass, Senegalese sole, gilt-head sea bream, red-banded seabream, common seabream, white seabream and wild meager; and
   wherein SJNNV is in the form of a heat killed or chemically inactivated SJNNV.

2. Vaccine as claimed in claim 1, wherein the SJNNV is SJNNV with a cDNA nucleotide sequence which is at least 95% identical with the nucleotide sequence of nucleotides 604 to 1030 of SEQ ID NO: 4.

3. Vaccine as claimed in claim 1, wherein the SJNNV is SJNNV with an amino acid sequence which is at least 95% identical with amino acid sequence of amino acids 204 to 331 SEQ ID NO: 5.

4. Vaccine as claimed in claim 1, wherein SJNNV is in an amount of at least about $1 \times 10^4$ TCID50/dose.

5. Vaccine as claimed in claim 1, wherein the SJNNV comprises a SJNNV RNA2 having a cDNA sequence of SEQ ID NO: 4.

6. Vaccine as claimed in claim 1, wherein chemically inactivated SJNNV is inactivated using binary ethyleneimine.

7. Vaccine comprising SJNNV nucleic acids; wherein the SJNNV nucleic acids are in the form of a DNA vaccine; and
   wherein the SJNNV nucleic acids comprise a cDNA sequence at least 95% identical with the nucleotide sequence of nucleotides 604 to 1030 of SEQ ID NO: 4.

8. Vaccine as claimed in claim 5, wherein the SJNNV further comprises a SJNNV RNA1 having a cDNA sequence of SEQ ID NO: 1.

9. A method for protecting fish against disease associated with red-spotted grouper nervous necrosis virus (RGNNV) infection, comprising administering an inactivated striped jack nervous necrosis virus (SJNNV) vaccine to a fish in need of protection from RGNNV infection;
   wherein the fish is selected from the group consisting of European sea bass, Senegalese sole, gilt-head sea bream, red-banded seabream, common seabream, white seabream and wild meager.

10. The method of claim 9, where the SJNNV vaccine comprises heat killed or chemically inactivated SJNNV comprising a SJNNV RNA1 having a cDNA sequence of SEQ ID NO: 1 and a SJNNV RNA2 having a cDNA sequence of SEQ ID NO: 4.

11. The method of claim 9, where the administering of the SJNNV vaccine is performed by intramuscular or peritoneal injection of the fish with the vaccine or immersion of fish in a bath containing the vaccine.

12. The method of claim 9, where an amount of the SJNNV administered to the fish is between about $1 \times 10^4$ and about $1.5 \times 10^4$ TCID50/fish.

13. The method of claim 9, where the administering of the SJNNV vaccine results in increased transcriptional expression of at least one interferon-inducible gene.

14. The method of claim 13, where the interferon-inducible gene includes Mx.

15. The method of claim 9, wherein the SJNNV vaccine is a DNA vaccine comprising a cDNA sequence at least 95% identical with nucleotides 604 to 1030 of SEQ ID NO: 4.

\* \* \* \* \*

UNITED STATES PATENT AND TRADEMARK OFFICE
CERTIFICATE OF CORRECTION

| | |
|---|---|
| PATENT NO. | : 9,884,103 B2 |
| APPLICATION NO. | : 14/888995 |
| DATED | : February 6, 2018 |
| INVENTOR(S) | : Juan Jose Borrego et al. |

It is certified that error appears in the above-identified patent and that said Letters Patent is hereby corrected as shown below:

On the Title Page

Item (72), Address for Inventor Jose Fernando Rodriguez, please delete "St. Catherina, Canada" and insert -- St. Catherines, PE, Canada --

Signed and Sealed this
Eleventh Day of December, 2018

Andrei Iancu
*Director of the United States Patent and Trademark Office*